(12) United States Patent
Miyamoto et al.

(10) Patent No.: US 7,662,349 B2
(45) Date of Patent: Feb. 16, 2010

(54) REACTOR

(75) Inventors: Naotomo Miyamoto, Tokyo (JP); Tadao Yamamoto, Tokyo (JP); Masaharu Shioya, Akiruno (JP)

(73) Assignee: Casio Computer Co., Ltd., Tokyo (JP)

( * ) Notice: Subject to any disclaimer, the term of this patent is extended or adjusted under 35 U.S.C. 154(b) by 343 days.

(21) Appl. No.: 11/513,486

(22) Filed: Aug. 31, 2006

(65) Prior Publication Data

US 2007/0055059 A1 Mar. 8, 2007

(30) Foreign Application Priority Data

Sep. 8, 2005 (JP) ............... 2005-260561

(51) Int. Cl.
*B01J 8/04* (2006.01)
*B01J 19/00* (2006.01)
*B01J 8/00* (2006.01)
*B01J 7/00* (2006.01)

(52) U.S. Cl. .............. 422/188; 422/189; 422/198; 422/199; 48/127.9; 48/61

(58) Field of Classification Search ............... 422/188, 422/189, 198, 199; 48/127.9, 61
See application file for complete search history.

(56) References Cited

U.S. PATENT DOCUMENTS 6,923,625 B2 * 8/2005 Sparks .................. 417/48

2004/0191591 A1 * 9/2004 Yamamoto .................. 429/19

FOREIGN PATENT DOCUMENTS

| JP | 11-326037 A | 11/1999 |
|----|-------------|---------|
| JP | 2002-356310 A | 12/2002 |
| JP | 2004-296349 A | 10/2004 |
| JP | 2004-303695 A | 10/2004 |
| JP | 2005-009553 A | 1/2005 |
| JP | 2005-132712 A | 5/2005 |

OTHER PUBLICATIONS

Japanese Office Action (and English translation thereof) dated Aug. 19, 2008, issued in a counterpart Japanese Application.

* cited by examiner

*Primary Examiner*—Walter D Griffin
*Assistant Examiner*—Lessanework Seifu
(74) *Attorney, Agent, or Firm*—Frishauf, Holtz, Goodman & Chick, P.C.

(57) ABSTRACT

Disclosed is a reactor including: a first reaction part and a second reaction part each comprising a reaction channel where a reactant flows, in which the reactant is applied to cause a reaction of the reactant, and which are arranged to form a gap therebetween; a heat insulating container covering at least entirety of the first reaction part, the second reaction part and the gap, in which a pressure within an inner space of the heat insulating container including the gap is lower than atmospheric pressure; and at least one getter material disposed in a space including the gap in the inner space. The getter material improves degree of vacuum in the inner space of the heat insulating container, and is disposed at the gap between the first reaction part and the second reaction part so as not to increase the size of the reactor.

27 Claims, 21 Drawing Sheets

REACTOR

CROSS-REFERENCE TO RELATED APPLICATIONS

This application is based upon and claims the benefit of priority from prior Japanese Patent Application No. 2005-260561, filed on Sep. 8, 2005, the entire contents of which are incorporated herein by reference.

BACKGROUND OF THE INVENTION

1. Field of the Invention

The present invention relates to a reactor to cause reaction of a reactant, particularly to a reactor comprising a vacuum heat insulating structure.

2. Description of Related Art

In recent years, a research and development for putting a fuel cell into practice has been greatly promoted as a clean power supply with high energy conversion efficiency for equipping the fuel cell with vehicles, portable equipment and the like. The fuel cell is equipment to allow a fuel to electrochemically react with oxygen in the air for directly extracting electric energy from chemical energy. Also, a research and development for downsizing a power source system using the fuel cell has been promoted to enable the power source system to be applied to a cell phone, electric vehicle and the like as a power source unit.

As a fuel used for the fuel cell, simple hydrogen can be given. There is a problem in handling hydrogen because simple hydrogen is a gas at ordinary temperature and pressure. Although there has been an attempt to store hydrogen with a hydrogen absorbing alloy, the storage amount of hydrogen per unit volume has been small and insufficient especially as a fuel storage unit for a power supply of compact electronic equipment such as portable electronic equipment.

On the other hand, a reformer fuel cell which reforms a liquid fuel having hydrogen atoms in the composition thereof such as alcohols and gasoline and utilizes the generated hydrogen can easily keep a fuel in a liquid state. Such a power source system comprising a reformer fuel cell may require a reactor comprising a reaction container such as a vaporizer for vaporizing a liquid fuel and water, a reformer for extracting hydrogen necessary for power generation by reacting a vaporized liquid fuel with a high-temperature water vapor, a carbon monoxide remover for removing carbon monoxide which is a by-product of the reforming reaction, and the like.

To downsize such a reactor, microreactors have been developed in which a vaporizer, reformer, and carbon monoxide remover are stacked up, and a groove is formed by joining a metal substrate so as to work as a reaction channel to cause the above-described various reactions.

An operating temperature of a vaporizer and carbon monoxide remover has less than 200° C., and that of a reformer is 250° C. or more. In order to keep the temperature, to ensure safety by preventing heat in a reformer and carbon monoxide remover leaking outside and to improve heat efficiency by reducing loss of heat energy, a container to make vacuum condition around a reformer and monoxide remover may be installed to be a vacuum heat insulating structure.

To form such a vacuum heat insulating structure, an insulating container to cover the reformer and carbon monoxide remover is provided and the inner space of the insulating container becomes vacuum condition. However, such vacuum insulation structure has a problem such that a leak is caused on the insulating container through a gap or the like formed in the production and air breaks in from outside, and that residual gas molecule absorbed on a surface of each reaction container or inner surface of the insulating container is released. In such case, vacuum around a reformer and carbon monoxide remover is down to decrease insulation property, so that heat leaks outside and heat loss increases. It is known to provide a getter material to inside of the insulating container to improve degree of vacuum of the inner space. However, because a certain volume is required to install a getter material, there is a problem that the getter material obstructs downsizing of the reactor.

SUMMARY OF THE INVENTION

In a reactor comprising vacuum heat insulating structure, the present invention is advantageous in that degree of vacuum in an insulating container is improved while the reactor is downsized.

In order to attain the above-described advantages, according to a first aspect of the invention, a reactor comprises: a first reaction part and a second reaction part each comprising a reaction channel where a reactant flows, in which the reactant is applied to the first reaction part and the second reaction part to cause a reaction of the reactant, and the first reaction part and the second reaction part are arranged to form a gap therebetween; a heat insulating container covering at least entirety of the first reaction part, the second reaction part and the gap, in which a pressure within an inner space of the heat insulating container including the gap is lower than atmospheric pressure; and at least one getter material disposed in a space including the gap in the inner space of the heat insulating container.

Preferably, the heat insulating container comprises a box formed by joining a sheet-like metal material, each of the first reaction part and the second reaction part comprises a reaction container of a rectangular parallelepiped, and the reaction channel is formed by providing a partition wall to inside of the reaction container, and the reaction container and the partition wall are formed by joining a sheet-like metal material.

Preferably, the first reaction part, the second reaction part and the heat insulating container are box-shaped, one face of the first reaction part is opposed to one face of the second reaction part, and the getter material is disposed to at least one position of an inner face of the heat insulating container corresponding to the gap, the opposed face of the first reaction part, and the opposed face of the second reaction part.

Preferably, the first reaction part is set to a first temperature, and the second reaction part is set to a second temperature which is lower than the first temperature, the reactor further comprises a heating part to heat the first reaction part and the second reaction part, the heating part is disposed to the first reaction part, heats the first reaction part to the first temperature, and heats the second reaction part to the second temperature via the connection part. Preferably, the heating part comprises a combustor including a catalyst for combustion to promote combustion reaction of the gas fuel to combust a gas fuel.

Preferably, the getter material is provided with a heater to heat the getter material so as to activate the getter material, the heater comprises an electric heating wire and a lead wire to supply electric power to the electric heating wire, and the lead wire is wired to penetrate the heat insulating container to reach outside. Preferably, the reactor comprises a cutting means to cut off the lead wire, for example by applies overcurrent to the lead wire so as to burn off the lead wire, at a position between any one face of the first reaction part or the second reaction part and an inner face of the heat insulating container, after the getter material is heated to be activated.

In order to attain the above-described advantages, according to a second aspect of the invention, a reactor comprises: a first reaction part and a second reaction part each comprising a reaction channel where a reactant flows, in which the reactant is applied to the first reaction part and the second reaction part to cause a reaction of the reactant, and the first reaction part and the second reaction part are box-shaped and are arranged to form a gap therebetween; a heat insulating container covering at least entirety of the first reaction part, the second reaction part and the gap, in which the heat insulating container has a rectangular parallelepiped shape and a pressure within an inner space of the heat insulating container including the gap is lower than atmospheric pressure; and at least one getter material disposed to at least one position of an inner face of the heat insulating container corresponding to the gap, a face of the first reaction part, and a face of the second reaction part, in which the face of the first reaction part is opposed to the face of the second reaction part.

Preferably, the heat insulating container comprises a box formed by joining a sheet-like metal material, each of the first reaction part and the second reaction part comprises a reaction container of a rectangular parallelepiped, and the reaction channel is formed by providing a partition wall to inside of a reaction container, and the reaction container and the partition wall are formed by joining a sheet-like metal material.

Preferably, the getter material is provided with a heater to heat the getter material so as to activate the getter material, the heater comprises an electric heating wire and a lead wire to supply electric power to the electric heating wire, and the lead wire is wired to penetrate the heat insulating container to reach outside.

In order to attain the above-described advantages, according to a third aspect of the invention, a reactor comprises: first reaction part and a second reaction part each comprising a reaction channel where a reactant flows, in which the reactant is applied to the first reaction part and the second reaction part to cause a reaction of the reactant, and the first reaction part and the second reaction part are arranged to form a gap therebetween; a heat insulating container covering at least entirety of the first reaction part, the second reaction part and the gap, in which an inner space of the heat insulating container including the gap has lower pressure than atmospheric pressure; and at least one getter material disposed in a space including the gap in the inner space of the heat insulating container, wherein the first reaction part is set to first temperature, and a first reactant is supplied to the first reaction part to form a first product, the second reaction part is set to second temperature which is lower than the first temperature, and the first product is supplied to the second reaction part to form a second product, the first reactant is gas mixture of vaporized water and a fuel whose composition contains a hydrogen atom, and the first reaction part is a reformer to cause a reforming reaction of the first reactant, and the first product contains carbon monoxide, and the second reaction part is a carbon monoxide remover to remove the carbon monoxide contained in the first product by selective oxidation.

Preferably, the reactor further comprises a vaporizer, wherein water and a liquid fuel whose composition contains hydrogen atom are supplied to the vaporizer, and the vaporizer vaporizes the water and the liquid fuel to form the gas mixture.

Preferably, the reactor further comprises: a connection part disposed at the gap, to transport the reactant and a product formed by the reaction between the first reaction part and the second reaction part; and a heating part, for example a combustor to combust a gas fuel, disposed to the first reaction part, to heat the first reaction part to the first temperature, wherein the heating part heats the second reaction part to the second temperature via the connection part.

DETAILED DESCRIPTION OF THE PREFERRED EMBODIMENTS

Figure 1:
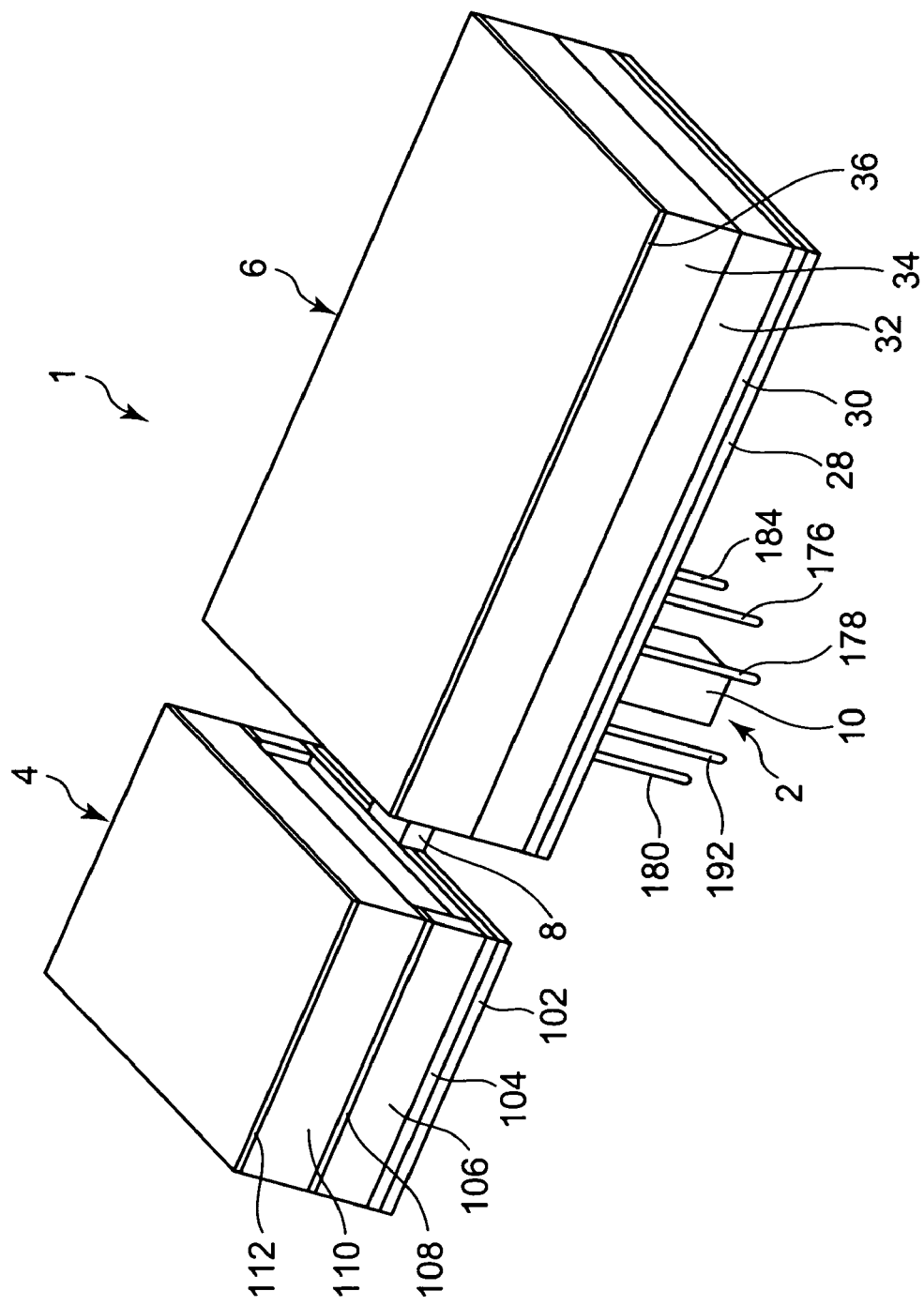
FIG. 1 is a perspective view of a microreactor module 1 in the embodiment reactor of the present invention seen from diagonally above.

Hereinafter, details of the reactor of the present invention will be described in detail based on the embodiments shown in the drawings.

Although there are various technically preferable limitations for implementation of the invention in the following embodiment, they are not for limiting the scope of the invention to the embodiment or examples illustrated as below.

FIG. 1 is a perspective view of a microreactor module 1 in the embodiment of the reactor of the present invention viewing from diagonally above.

Figure 2:
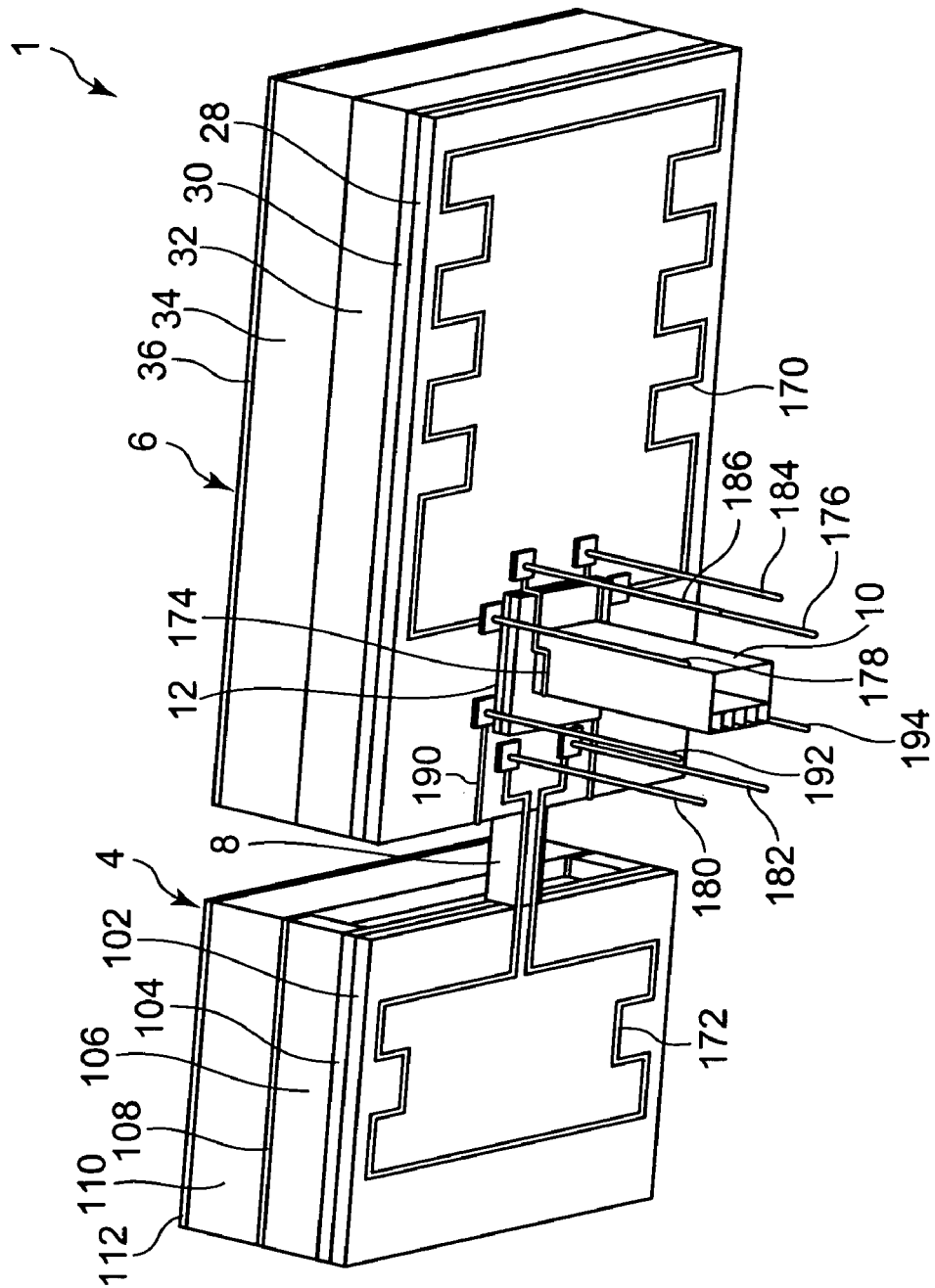
FIG. 2 is a perspective view of the microreactor module 1 of the present embodiment shown from diagonally below.

FIG. 2 is a perspective view of the microreactor module 1 in the present embodiment viewing from diagonally below.

Figure 3:
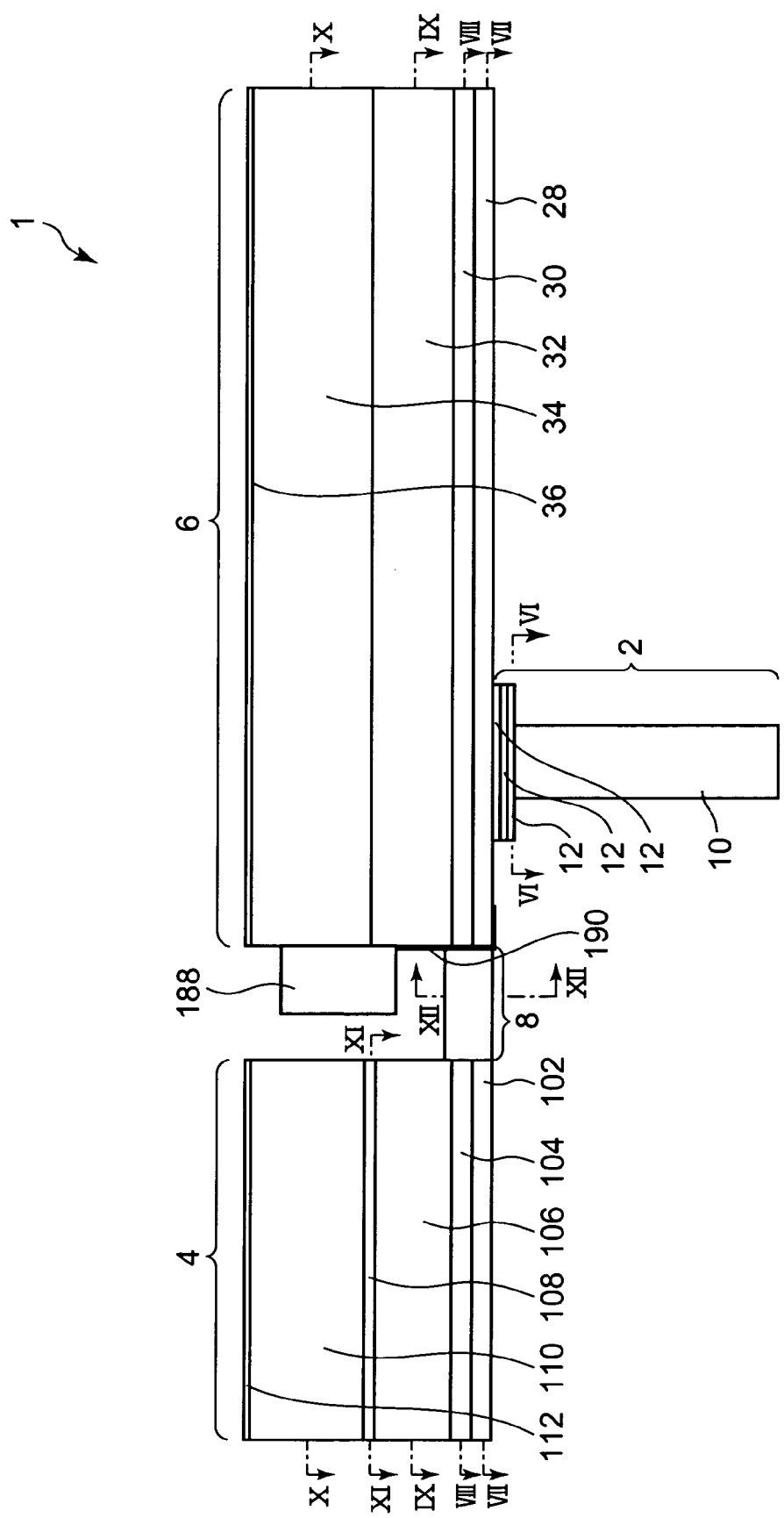
FIG. 3 is a side view of the microreactor module 1 of the present embodiment.

FIG. 3 is a side view of the microreactor module 1 in the present embodiment.

The microreactor module 1 is a reactor built into electronic equipment such as a notebook personal computer, PDA, electronic organizer, digital camera, cellular phone, wrist watch, register, and projector for generating a hydrogen gas used for a fuel cell.

The microreactor module 1 includes a supply and discharge part 2 in which reactants are supplied and products are discharged, a high-temperature reaction part (a first reaction part) 4 in which a reforming reaction occurs at relatively high temperature, the low-temperature reaction part (a second reaction part) 6 in which a selective oxidation reaction occurs at lower temperature than the temperature in the high-temperature reaction part 4, and a connecting pipe (connecting part) 8 for flowing in or flowing out the reactants and products between the high-temperature reaction part 4 and the low-temperature reaction part 6.

Figure 4:
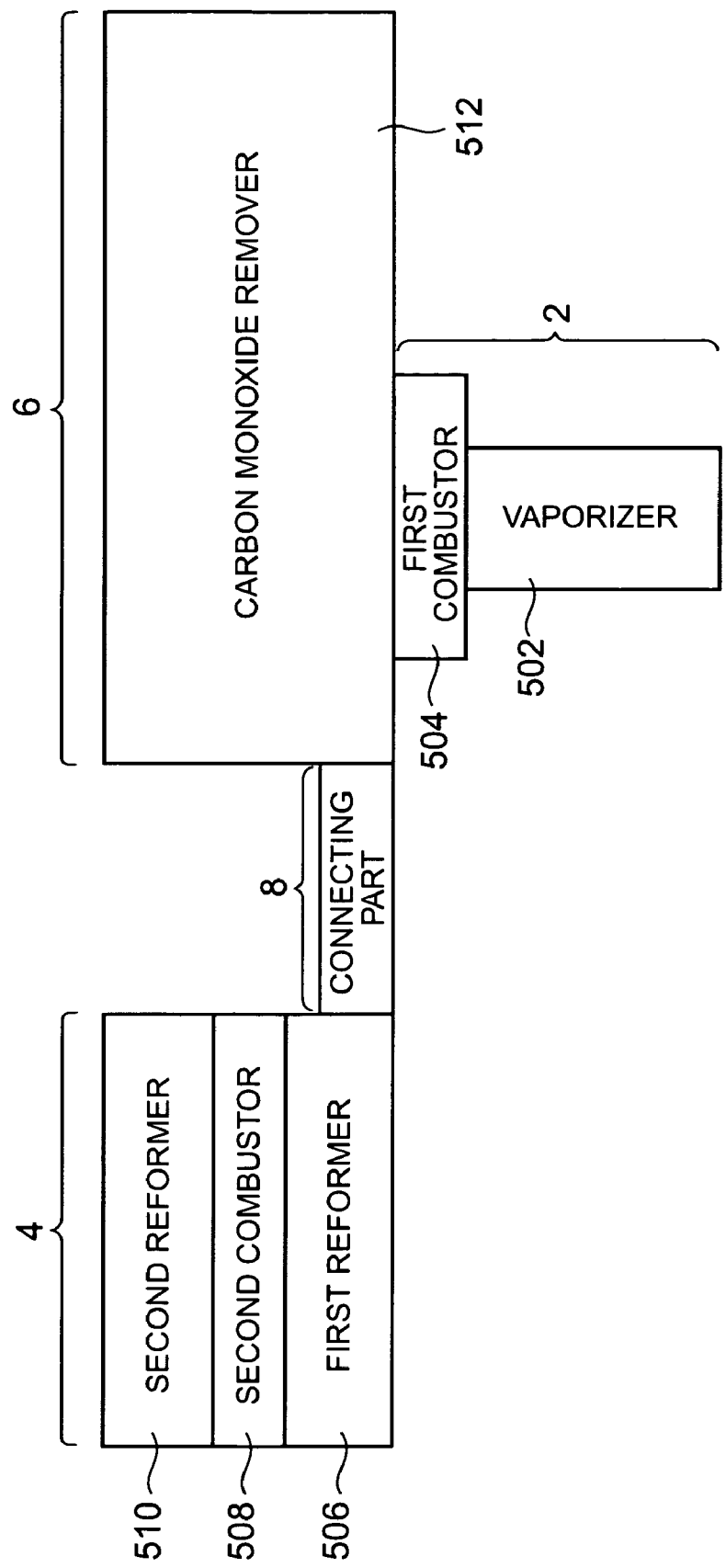
FIG. 4 is a schematic side view when the microreactor module 1 of the present embodiment is divided with respect to each function.

FIG. 4 is a schematic side view when the microreactor module 1 of the present embodiment is divided with respect to each function.

As shown in FIG. 4, the supply and discharge part 2 is mainly provided with a vaporizer 502 and a first combustor 504. To the first combustor 504, air and a gas fuel (e.g., hydrogen gas, methanol gas, or the like) are supplied separately or as gas mixture, and catalytic combustion of these gases generates heat. To the vaporizer 502, water and a liquid fuel (e.g., methanol, ethanol, dimetyl ether, butane, gasoline) are supplied separately or as mixture from a fuel container, and the water and the liquid fuel vaporize within the vaporizer 502 due to the combustion heat in the first combustor 504.

The high-temperature reaction part 4 is provided with a first reformer (a first reactor) 506, a second combustor (heating part) 508, and a second reformer (a second reactor) 510. For example, they are arranged so that the second combustor 508 is sandwiched between the first reformer 506 located at the lower side and the second reformer 510 located at the upper side.

To the second combustor 508, air and a gas fuel (e.g., hydrogen gas, methanol gas, or the like) are supplied separately or as mixture, and catalytic combustion of these gases generates heat. It is preferable that electricity is generated by electrochemical reaction of hydrogen gas in a fuel cell, and unreacted hydrogen gas contained in the offgas discharged from the fuel cell is provided to the first combustor 504 and the second combustor 508 in a state where the hydrogen gas is mixed with air. Further, it is also preferable that the liquid fuel (e.g., methanol, ethanol, dimetyl ether, butane, or gasoline) stored in the fuel container is vaporized with another vaporizer and mixture of the vaporized fuel with air may be provided in the first combustor 504 and the second combustor 508.

Gas mixture of a liquid fuel and water vaporized from the vaporizer 502 (the first reactant) is provided to the first reformer 506 and the second reformer 510. The second combustor 508 heats the first reformer 506 and the second reformer 510. In the first reformer 506 and the second reformer 510, hydrogen gas and the like (the first reaction product) are generated by catalytic reaction of water vapor and a vaporized liquid fuel, and carbon monoxide gas is further generated even though in a small amount. When the liquid fuel is methanol, chemical reactions as of following formulae (1) and (2) occur. The reaction of generating hydrogen is an endothermic reaction, and the combustion heat of the second combustor 508 is used thereto.

$$CH_3OH + H_2O \rightarrow 3H_2 + CO_2 \qquad (1)$$

$$2CH_3OH + H_2O \rightarrow 5H_2 + CO + CO_2 \qquad (2)$$

The low-temperature reaction part 6 is mainly provided with a carbon monoxide remover 512. The first combustor 504 heats the carbon monoxide remover 512, and gas mixture (the second reactant) containing hydrogen gas, a small amount of carbon monoxide gas generated by the chemical reaction of above formula (2) and the like, and also air are supplied from the first reformer 506 and the second reformer 510 to the carbon monoxide remover 512. In the carbon monoxide remover 512, carbon monoxide is selectively oxidized among the gas mixture, and thereby, carbon monoxide is removed. The gas mixture (the second reaction product: hydrogen-rich gas) from which carbon monoxide has been removed is supplied to a fuel electrode of the fuel cell.

As below, specific configurations of the discharge part 2, the high-temperature reaction part 4, the low-temperature reaction part 6, and the connecting pipe 8 will be described using FIGS. 3 and 5 to 12.

Figure 5:
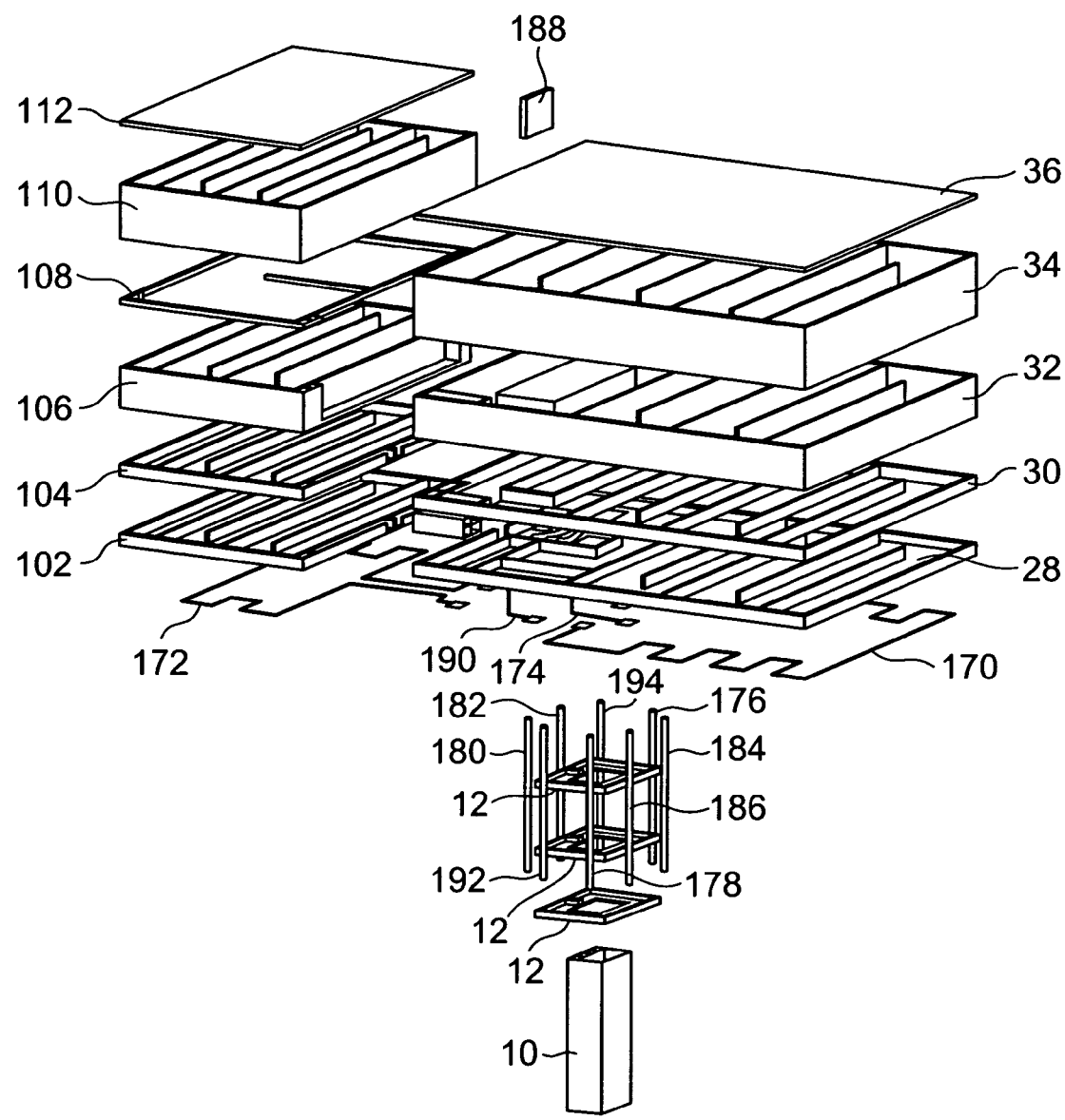
FIG. 5 is an exploded perspective view of the microreactor module 1 of the present embodiment.

FIG. 5 is an exploded perspective view of the microreactor module 1 in the present embodiment.

Figure 6:
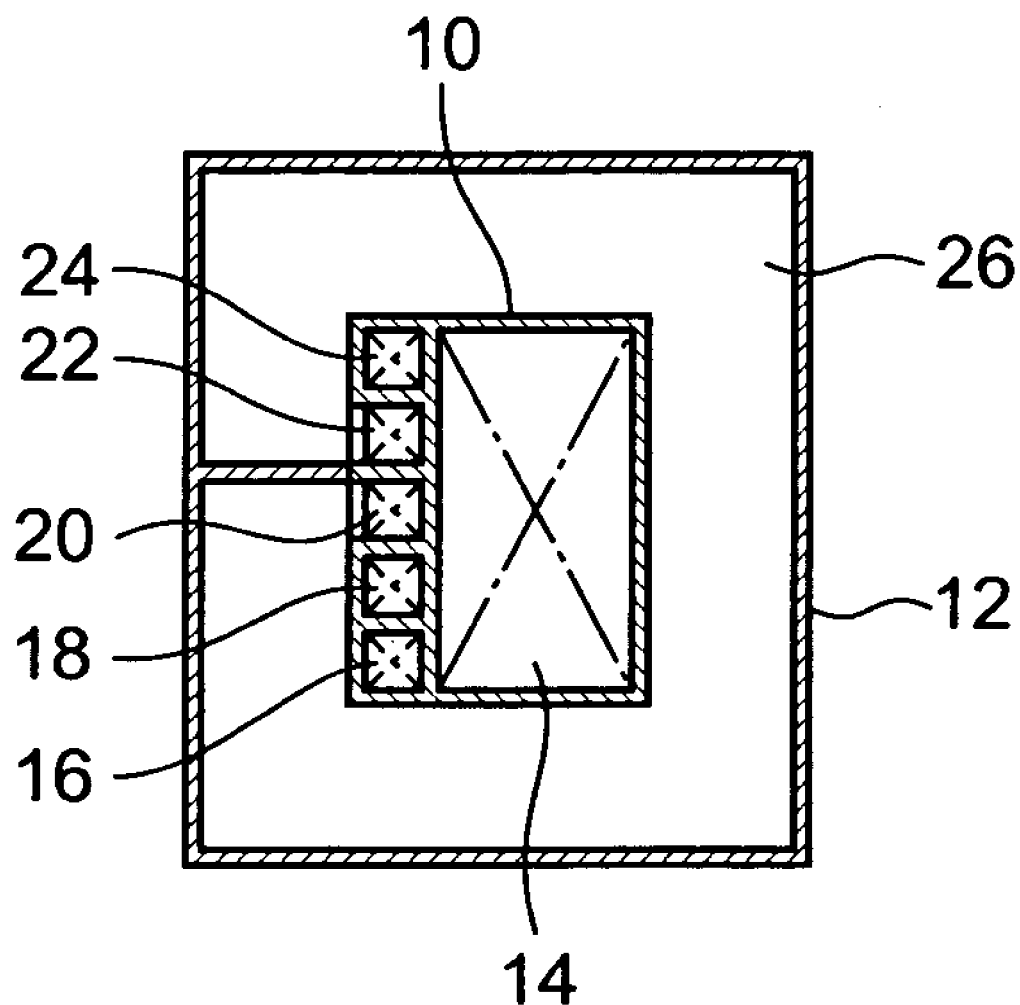
FIG. 6 is a sectional view in the direction of arrows in a plane along section line VI-VI in FIG. 3.

FIG. 6 is a sectional view in the direction of arrows taken along a direction of a plane of a combustor plate 12, which will be described later, from section line VI-VI in FIG. 3.

Figure 7:
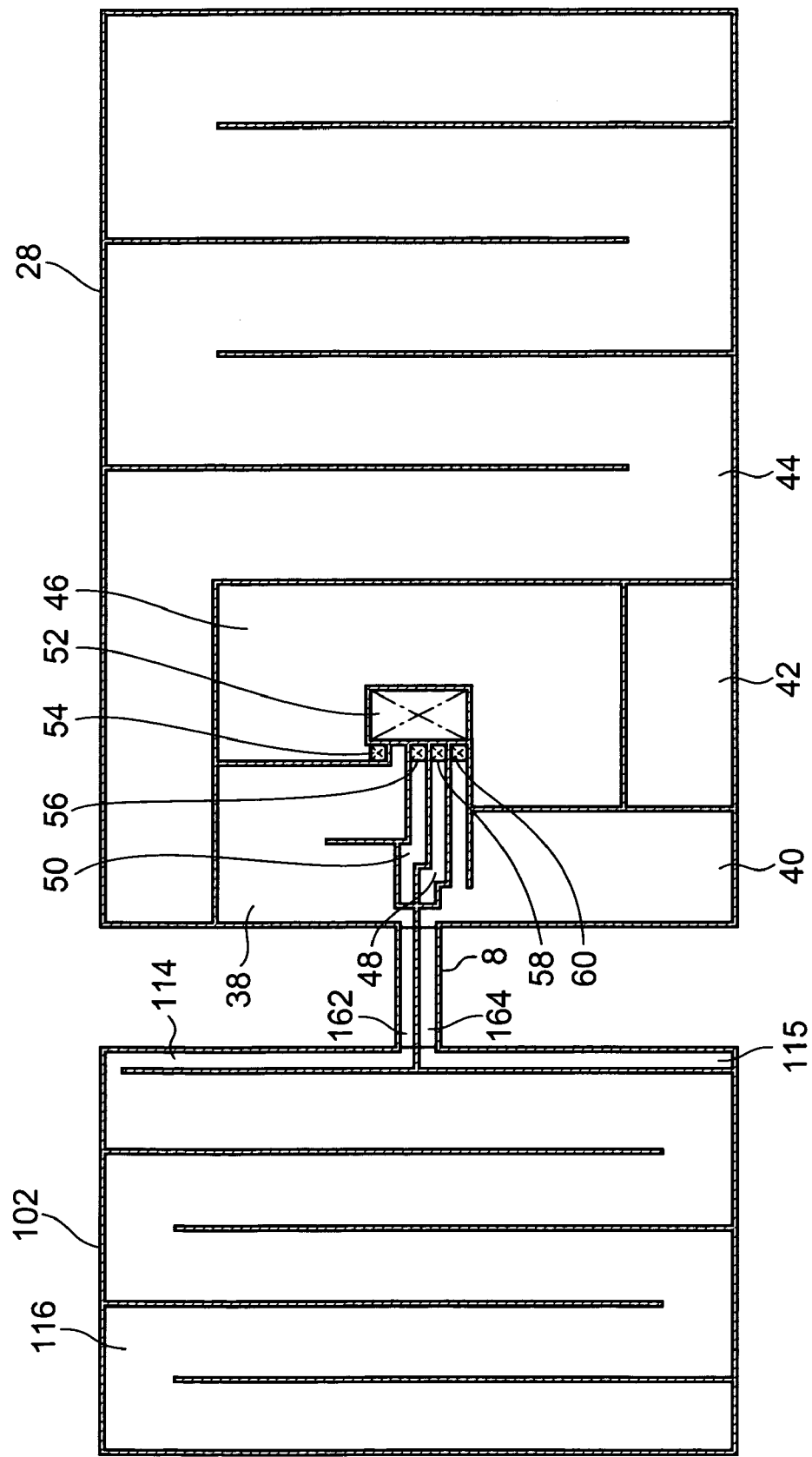
FIG. 7 is a sectional view in the direction of arrows in a plane along section line VII-VII in FIG. 3.

FIG. 7 is a sectional view in the direction of arrows taken along a direction of a plane of a base plate 28 and a base plate 102, which will be described later, from section line VII-VII in FIG. 3.

Figure 8:
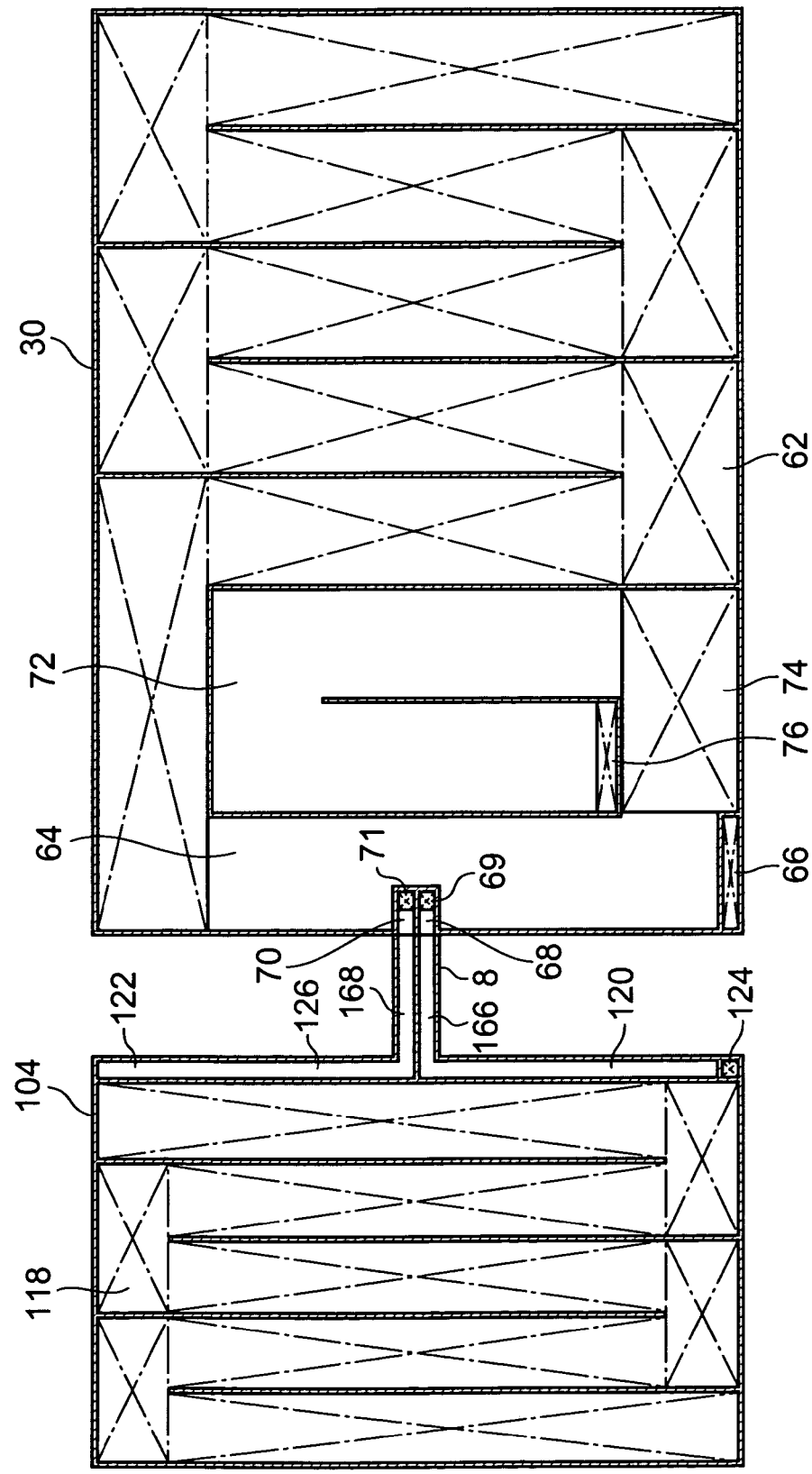
FIG. 8 is a sectional view in the direction of arrows in a plane along section line VIII-VIII in FIG. 3.

FIG. 8 is a sectional view in the direction of arrows taken along a direction of a plane of a lower frame 30 and a lower frame 104, which will be described later, from section line VIII-VIII in FIG. 3.

Figure 9:
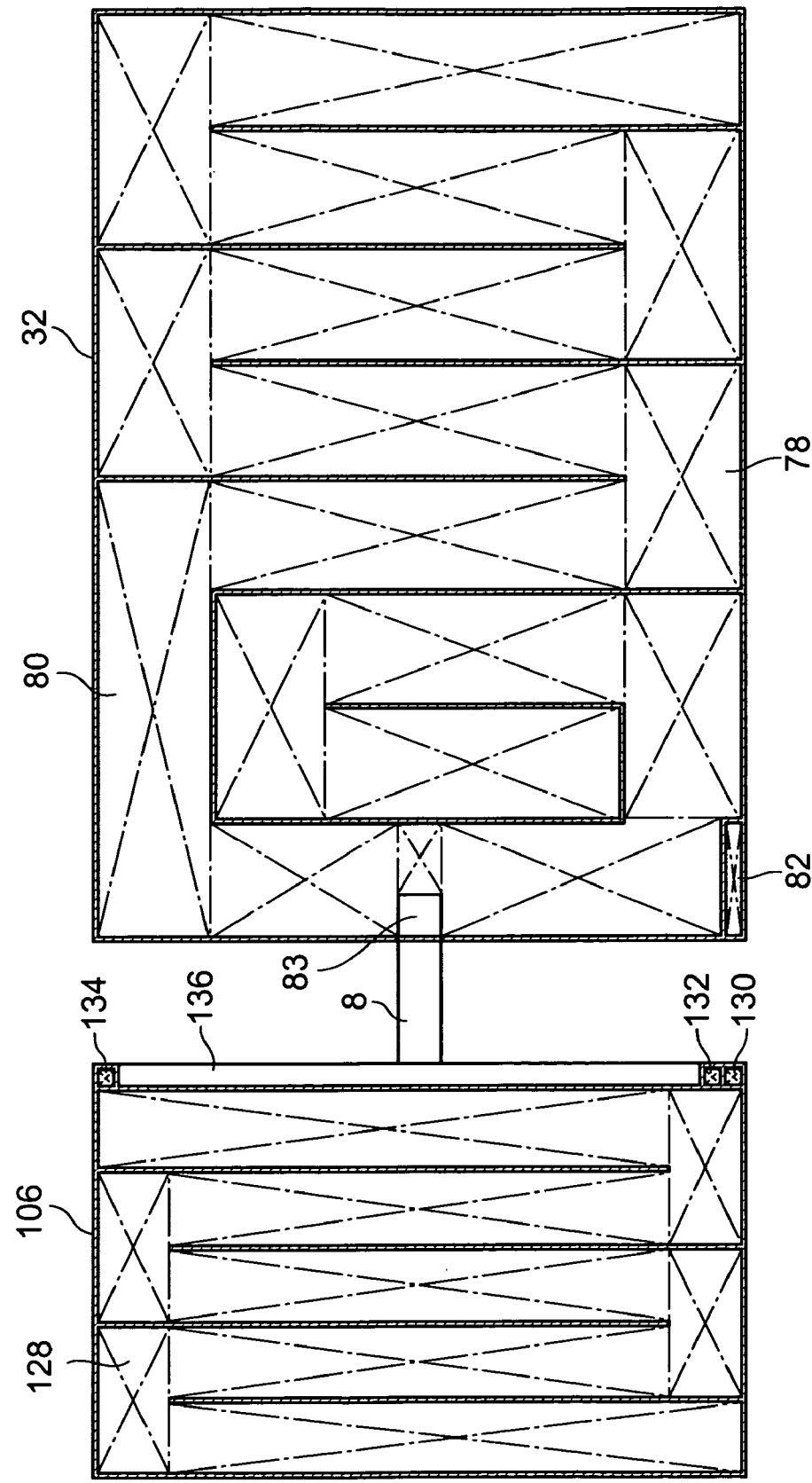
FIG. 9 is a sectional view in the direction of arrows in a plane along section line IX-IX in FIG. 3.

FIG. 9 is a sectional view in the direction of arrows taken along a direction of a plane of a middle frame 32 and a middle frame 106, which will be described later, from section line IX-IX in FIG. 3.

Figure 10:
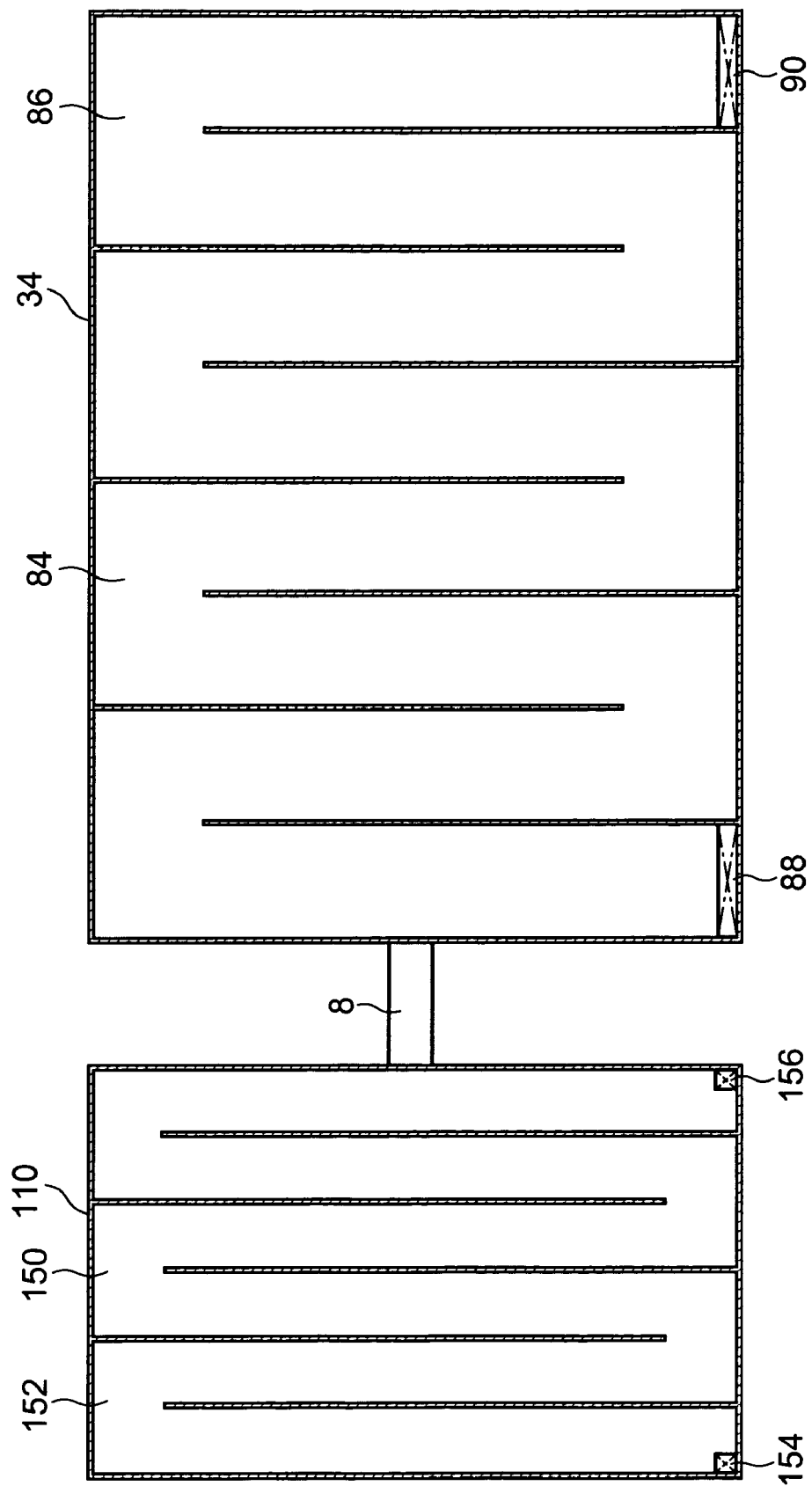
FIG. 10 is a sectional view in the direction of arrows in a plane along section line X-X in FIG. 3.

FIG. 10 is a sectional view in the direction of arrows taken along a direction of a plane of an upper frame 34 and an upper frame 110, which will be described later, from section line X-X in FIG. 3.

Figure 11:
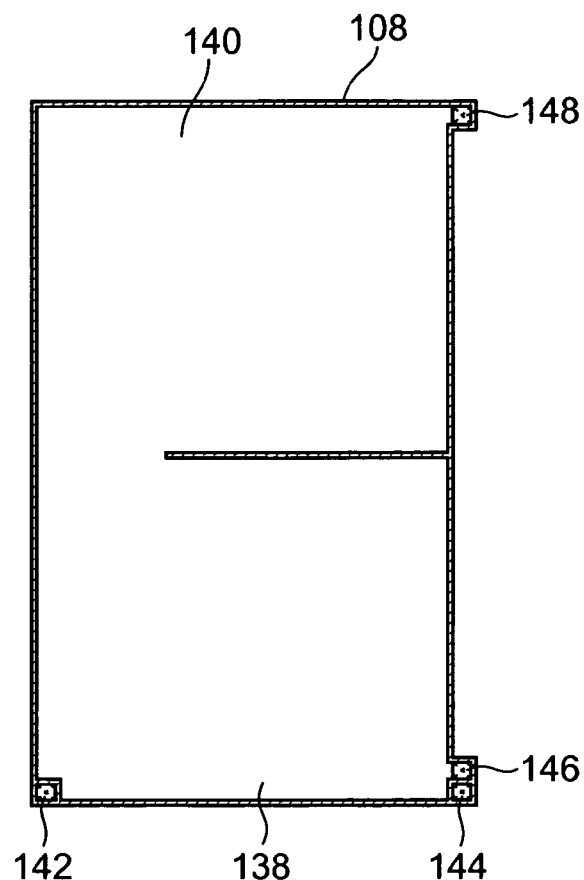
FIG. 11 is a sectional view in the direction of arrows in a plane along section line XI-XI in FIG. 3.

FIG. 11 is a sectional view in the direction of arrows taken along a direction of a plane of a combustor plate 108, which will be described later, from section line XI-XI in FIG. 3.

Figure 12:
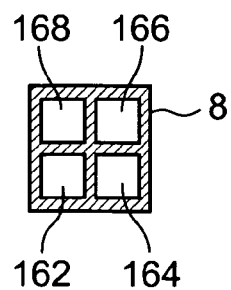
FIG. 12 is a sectional view in the direction of arrows in a plane along section line XII-XII in FIG. 3.

FIG. 12 is a sectional view in the direction of arrows taken along a direction of a plane perpendicular to the communication direction of the connecting pipe 8 from section line XII-XII in FIG. 3.

Figure 13:
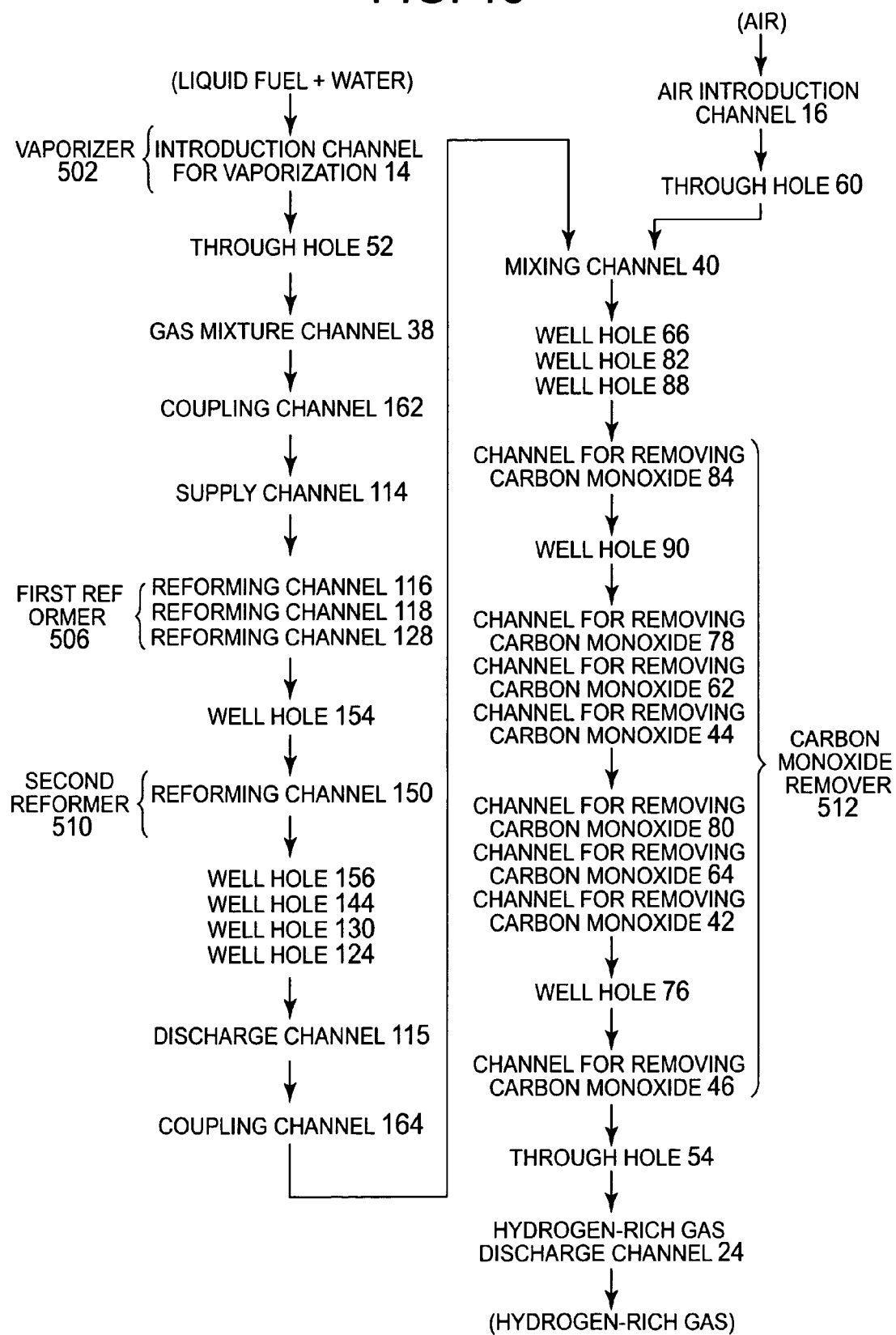
FIG. 13 shows a pathway from supply of a liquid fuel and water to discharge of hydrogen-rich gas as a product in the microreactor module of the present embodiment.

FIG. 13 is a view showing the pathway from supply of a liquid fuel and water to discharge of hydrogen-rich gas of a product in the microreactor module 1 in the present embodiment.

Figure 14:
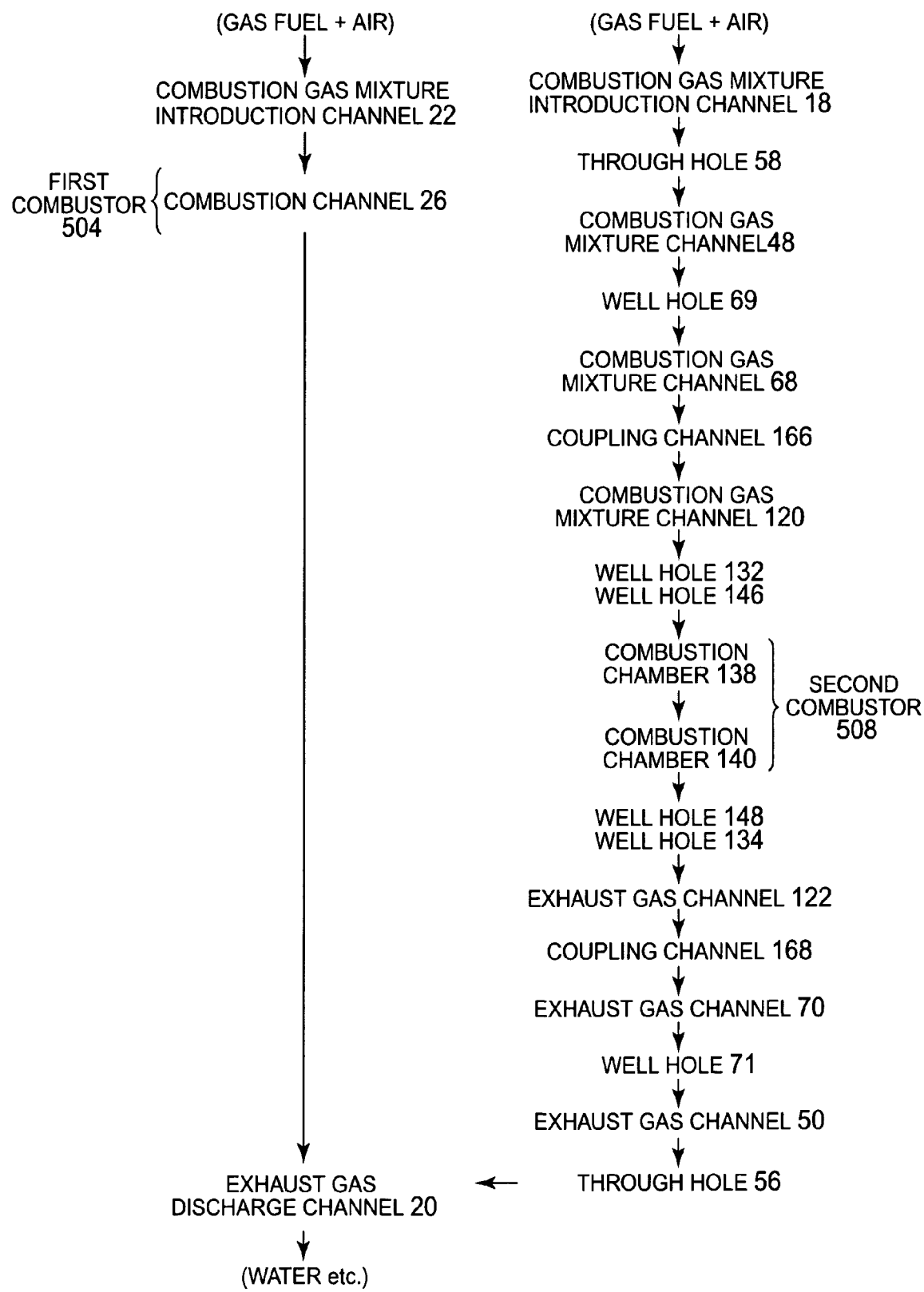
FIG. 14 shows a pathway from supply of combustion mixture to discharge of water and the like as products.

FIG. 14 is a view t showing the pathway from supply of combustion gas mixture comprising a gas fuel and air to discharge of a product such as water in the microreactor module 1 in the present embodiment.

As shown in FIGS. 3, 5, and 6, the supply and discharge part 2 has, for example, includes an external circulation pipe 10 made of a sheet-like metal material such as stainless steel and three combustion plates 12 stacked around the external circulation pipe 10.

The external circulation pipe 10 is a pipe having plural channels circulating the respective fluids within the microreactor module 1 to the outside of the microreactor module 1, and the external circulation pipe 10 is provided with an introduction channel for vaporization 14, an air introduction channel 16, a combustion mixture introduction channel 18, an exhaust gas discharge channel 20, a combustion mixture introduction channel 22, and a hydrogen discharge channel 24 in parallel with one another. The introduction channel for vaporization 14, the air introduction channel 16, the combustion mixture introduction channel 18, the exhaust gas discharge channel 20, the combustion mixture introduction channel 22, and the hydrogen gas discharge channel 24 are partitioned by partition walls of the external circulation pipe 10. Although the introduction channel for vaporization 14, the air introduction channel 16, the combustion mixture introduction channel 18, the exhaust gas discharge channel 20, the combustion mixture introduction channel 22, and the hydrogen gas discharge channel 24 are all provided in one external circulation pipe 10, these channels 14, 16, 18, 20, 22, 24 may be provided as separate tube materials and the external circulation pipe 10 may be formed by bundling the tube materials together.

The introduction channel for vaporization 14 is filled with a liquid absorbing material such as a felt material, ceramic porous material, fiber material, and carbon porous material. The liquid absorbing material is for absorbing a liquid, and may be a material such as an inorganic fiber or organic fiber hardened with a binder, a sintered inorganic powder, an inorganic powder hardened with a binder, or mixture of graphite and glassy carbon.

The combustor plate 12 is, for example, made of a sheet-like metal material such as stainless steel. A through hole is formed at the center of the combustor plate 12, and the external circulation pipe 10 is fitted in the through hole. The external circulation pipe 10 and the combustor plate 12 are jointed. The external circulation pipe 10 is jointed to the combustion plates 12 by brazing. As a brazing material, a solder having a melting point higher than the maximum temperature of the fluids flowing in the external circulation pipe 10 and the combustion plates 12 and 700° C. or more is preferably applied. Specifically, a gold solder containing silver, copper, zinc, and cadmium in gold, a solder mainly composed of gold, silver, zinc, and nickel, or a solder mainly composed of gold, palladium, and silver is especially preferable. Further, a partition wall is provided so as to project on one face of the combustor plate 12. Part of the partition wall is provided over the entire circumference of the outer rim of the combustor plate 12, the other part is provided in the radial direction. The three combustor plates 12 are stacked by brazing joint around the external circulation pipe 10 and the uppermost combustor plate 12 is joined to the lower face of the low-temperature reaction part 6, so that a combustion channel 26 is formed on the joined faces. One end of the combustion channel 26 leads to the combustion mixture introduction channel 22 and the other end of the combustion channel 26 leads to the exhaust gas discharge channel 20. On the wall of the combustion channel 26, a combustion catalyst for combusting the combustion mixture is supported. As the combustion catalyst, platinum or the like can be given. The external circulation pipe 10 is filled with the liquid absorbing material to the location of the combustor plate 12.

As shown in FIGS. 3 and 5, the low-temperature reaction part 6 is formed by stacking the base plate 28, the lower frame 30, the middle frame 32, the upper frame 34, and a lid plate 36 in this order from the bottom, and has a rectangular parallelepiped shape. The base plate 28, the lower frame 30, the middle frame 32, the upper frame 34, and the lid plate 36 are, for example, made of a sheet-like metal material such as stainless steel.

At the center in the width direction of the base plate 28, the external circulation pipe 10 and the uppermost combustor plate 12 are joined to the lower face of the base plate 28. As shown in FIG. 7, since a partition wall is provided so as to project on the upper face of the base plate 28, the channel is divided into a gas mixture channel 38, a mixing channel 40, a channel for removing carbon monoxide 42, a zig-zag channel for removing carbon monoxide 44, a U-shaped channel for removing carbon monoxide 46, a combustion mixture channel 48, and an exhaust gas channel 50. A through hole 52 is formed at the end of the gas mixture channel 38, and the gas mixture channel 38 leads to the introduction channel for vaporization 14 of the external circulation pipe 10 via the through hole 52. The channel for removing carbon monoxide 46 surrounds the through hole 52, and a through hole 54 is formed at the end of the channel for removing carbon monoxide 46 and the channel for removing carbon monoxide 46 leads to the hydrogen discharge channel 24 via the through hole 54. A through hole 58 is formed at the end of the combustion mixture channel 48 and the combustion mixture channel 48 leads to the combustion mixture introduction channel 18 via the through hole 58. A through hole 56 is formed at the end of the exhaust gas channel 50 and the exhaust gas channel 50 leads to the exhaust gas discharge channel 20 via the through hole 56. A through hole 60 is formed at the end of the mixing channel 40 and the mixing channel 40 leads to the air introduction channel 16 via the through hole 60.

As shown in FIG. 8, since a plurality of partition walls are provided inside of the lower frame 30, the interior of the lower frame 30 is divided into a zig-zag channel for removing carbon monoxide 62, a spiral channel for removing carbon monoxide 64, a well hole 66, a combustion mixture channel 68, and an exhaust gas channel 70. A bottom plate 72 is provided in the channel for removing carbon monoxide 64, the combustion mixture channel 68, and the exhaust gas channel 70. When the lower frame 30 is joined on the base plate 28 by brazing or the like, the upper part of the gas mixture channel 38, the mixing channel 40, the channel for removing carbon monoxide 46, the combustion mixture channel 48, and the exhaust gas channel 50 are covered with the bottom plate 72. Further, one end 64a of the channel for removing carbon monoxide 64 leads to the channel for removing carbon monoxide 62, a well hole 74 which leads to the channel for removing carbon monoxide 42 of the base plate 28 is formed in the middle of the channel for removing carbon monoxide 64, and a well hole 76 which leads to the exhaust gas channel 50 of the base plate 28 is formed at the other end of the channel for removing carbon monoxide 64. The channel for removing carbon monoxide 62 is overlapped with the channel for removing carbon monoxide 44 of the base plate 28, and the channel for removing carbon monoxide 62 and channel for removing carbon monoxide 44 are connected each other. The well hole 66 is located above the mixing channel 40 of the base plate 28. A well hole 69 is formed in the combustion mixture channel 68 and the combustion mixture channel 68 leads to the combustion mixture channel 48 of the base plate 28 via the well hole 69. A well hole 71 is formed in the exhaust gas channel 70 and the exhaust gas channel 70 leads to the exhaust gas channel 50 of the base plate 28 via the well hole 71. In a plain view, the external circulation pipe 10 is overlapped with a part of the channel for removing carbon monoxide 64 which swirls around the external circulation pipe 10.

As shown in FIG. 9, since a partition wall is provided inside of the middle frame 32, the interior of the middle frame 32 is divided into a zig-zag channel for removing carbon monoxide 78, a spiral channel for removing carbon monoxide 80, and a well hole 82.

A bottom plate 83 is provided in part of the channel for removing carbon monoxide 80. When the middle frame 32 is joined to the lower frame 30 by brazing or the like, the upper part of the combustion mixture channel 68 and the exhaust gas channel 70 of the lower frame 30 is covered with the bottom plate 83.

The channel for removing carbon monoxide 78 is overlapped with the channel for removing carbon monoxide 62 of the lower frame 30 so that the channel for removing carbon monoxide 78 is connected with the channel for removing carbon monoxide 62 of the lower frame 30, and the channel for removing carbon monoxide 62 form a well.

The channel for removing carbon monoxide 80 is overlapped with and is connected with the channel for removing carbon monoxide 64 of the lower frame 30. The well hole 82 is overlapped with the well hole 66 of the lower frame 30, and the well hole 82 and the well hole 66 are in communication with each other.

As shown in FIG. 10, a plurality of partition walls are provided inside of the upper frame 34 so that a zig-zag channel for removing carbon monoxide 84 is formed inside of the upper frame 34. Further, a bottom plate 86 is provided in the entire interior of the upper frame 34. When the upper frame 34 is joined to the middle frame 32 by brazing or the like, the upper part of the channel for removing carbon monoxide 78 and the channel for removing carbon monoxide 80 of the middle frame 32 is covered with the bottom plate 86. Further, a well hole 88 is formed at one end of the channel for removing carbon monoxide 84 and a well hole 90 is formed at the other end of the channel for removing carbon monoxide 84. The well hole 88 is overlapped with the well hole 82 of the middle frame 32, and the channel for removing carbon monoxide 84 leads to the mixing channel 40 via the well hole 88, the well hole 82, and the well hole 66. The well hole 90 is located above the end of the channel for removing carbon monoxide 78 of the middle frame 32 and the channel for removing carbon monoxide 84 leads to the channel for removing carbon monoxide 78 via the well hole 90.

As shown in FIG. 5, since the lid plate 36 is joined to the upper part of the upper frame 34, the upper part of the channel for removing carbon monoxide 84 is covered by the lid plate 36. Here, catalysts for selective oxidization of carbon monoxide for selectively oxidizing carbon monoxide is supported on the entire wall surfaces of the channels for removing carbon monoxide 42, 44, 46, 62, 64, 78, 80, and 84. As the catalyst for selective oxidization of carbon monoxide, platinum or the like can be given.

As shown in FIGS. 3 and 5, the high-temperature reaction part 4 is formed by stacking the base plate 102, the lower frame 104, the middle frame 106, the combustor plate 108, the upper frame 110, and the lid plate 112 in this order from the bottom and has a rectangular parallelepiped shape. The base plate 102, the lower frame 104, the middle frame 106, the combustor plate 108, the upper frame 110, and the lid plate 112 are made of a sheet-like metal material such as stainless steel.

As shown in FIG. 7, since a plurality of partition walls are provided on the upper face of the base plate 102 so as to be projected, the channel is divided into a supply channel 114, a zig-zag reforming channel 116, and a discharge channel 115. The supply channel 114 continues to the reforming channel 116, and the discharge channel 115 is separated from the supply channel 114 and the reforming channel 116.

As shown in FIG. 8, since a plurality of partition walls are provided inside of the lower frame 104, the interior of the lower frame 104 is divided into a zig-zag reforming channel 118, a combustion mixture channel 120, an exhaust gas channel 122, and a well hole 124. A bottom plate 126 is provided in the combustion mixture channel 120 and the exhaust gas channel 122. When the lower frame 104 is joined to the base plate 102 by brazing or the like, the supply channel 114 and the discharge channel 115 of the base plate 102 are covered with the bottom plate 126. The reforming channel 118 is overlapped with the reforming channel 116 of the base plate 102, the reforming channel 118 and the reforming channel 116.

As shown in FIG. 9, since a plurality of partition walls are provided inside of the middle frame 106, the interior of the middle frame 106 is divided into a zig-zag reforming channel 128, a well hole 130, a well hole 132, and a well hole 134. A bottom plate 136 is provided in the middle frame 106. When the middle frame 106 is joined to the lower frame 104 by brazing or the like, the upper part of the combustion mixture channel 120 and the exhaust gas channel 122 of the lower frame 104 are covered with the bottom plate 136. The reforming channel 128 is overlapped with the reforming channel 118 of the lower frame 104, and the reforming channel 128 and the reforming channel 118 are in communication with each other. The well hole 130 is overlapped with the well hole 124 of the lower frame 104 and the well hole 130 and the well hole 124 are in communication with each other. The well hole 132 is located above the end of the combustion mixture channel 120, and the well hole 134 is located above the end of the exhaust gas channel 122.

As shown in FIGS. 3 and 5, since the combustor plate 108 is joined to the upper part of the middle frame 106 by brazing or the like, the upper part of the reforming channel 128 of the middle frame 106 is covered with the combustor plate 108. As shown in FIG. 11, since a partition wall is provided so as to be projected on the upper face of the combustor plate 108, the channel is divided into a combustion chamber 138, a combustion chamber 140, a well hole 142, and a well hole 144. A well hole 146 is formed at the end of the combustion chamber 138, the well hole 146 is located above the well hole 132 of the middle frame 106, and the combustion chamber 138 leads to the combustion mixture channel 120 of the lower frame 104 via the well hole 146 and the well hole 132. The combustion chamber 138 leads to the combustion chamber 140. Further, a well hole 148 is formed at the end of the combustion chamber 140, the well hole 148 is located above the well hole 134 of the middle frame 106, and the combustion chamber 140 leads to the exhaust gas channel 122 via the well hole 148 and the well hole 134. The well hole 142 is located above the end of the reforming channel 128 of the middle frame 106 and the well hole 142 leads to the reforming channel 128. The well hole 144 is located above the well hole 130 of the middle frame 106 and the well hole 144 leads to the well hole 130. Catalysts for combustion for combusting the combustion mixture are supported on the wall surfaces of the combustion chamber 138 and the combustion chamber 140. As the catalyst for combustion, platinum or the like can be given.

As shown in FIG. 10, since a plurality of partition walls are provided inside of the upper frame 110, a zig-zag reforming channel 150 is formed inside of the upper frame 110. Further, a bottom plate 152 is provided in the upper frame 110. When the upper frame 110 is joined to the upper part of the combustor plate 108 by brazing or the like, the upper part of the combustion chamber 138 and the combustion chamber 140 of the combustor plate 108 is covered. A well hole 154 is formed at one end of the reforming channel 150 and a well hole 156 is formed at the other end of the reforming channel 150. The well hole 154 is located above the well hole 142 of the combustor plate 108, and the reforming channel 150 leads to the reforming channel 128 of the middle flame 106 via the well hole 154 and the well hole 142. The well hole 156 is located above the well hole 144 of the combustor plate 108, and the reforming channel 150 leads to the discharge channel 115 via the well hole 156, the well hole 144, the well hole 130, and the well hole 124.

As shown in FIG. 5, since the lid plate 112 is joined to the upper part of the upper frame 110 by brazing or the like, the upper part of the reforming channel 150 is covered with the lid plate 112. Here, catalysts for reforming which reforms the fuel to generate hydrogen are supported on the wall surfaces of the supply channel 114, the discharge channel 115, and the reforming channels 116, 118, 128, and 150. As the catalyst used for reforming methanol, for example, Cu/ZnO catalyst, Pd/ZnO catalyst, or the like can be given.

As shown in FIGS. 3 and 4, the outer shape of the connecting pipe 8 takes rectangular column, the width of the connecting pipe 8 is narrower than the width of the high-temperature reaction part 4 and the low-temperature reaction part 6, and the height of the connecting pipe 8 is lower than the heights of the high-temperature reaction part 4 and the low-temperature reaction part 6. The connecting pipe 8 is spanned between the high-temperature reaction part 4 and the low-temperature reaction part 6, and the connecting pipe 8 is joined by brazing or the like to the high-temperature reaction part 4 at the center in the width direction of the high-temperature reaction part 4 and also joined by brazing or the like to the low-temperature reaction part 6 at the center in the width direction of the low-temperature reaction part 6. Further, the lower face of the connecting pipe 8 is flush with the lower face of the high-temperature reaction part 4, i.e., the lower face of the base plate 102 and also flush with the lower face of the low-temperature reaction part 6, i.e., the lower face of the base plate 28.

As shown in FIGS. 7, 8, and 12, the connecting pipe 8 is provided with a coupling channel 162, a coupling channel 164, a coupling channel 166, and a coupling channel 168 which are in parallel with one another. The coupling channel 162, the coupling channel 164, the coupling channel 166, and the coupling channel 168 are partitioned by partition walls of the connecting pipe 8. One end of the coupling channel 162 leads to the gas mixture channel 38 and the other end of the coupling channel 162 leads to the supply channel 114. One end of the coupling channel 164 leads to the discharge channel 115 and the other end of the coupling channel 164 leads to the mixing channel 40. One end of the coupling channel 166 leads to the combustion mixture channel 68 and the other end of the coupling channel 166 leads to the combustion mixture channel 120. One end of the coupling channel 168 leads to the exhaust gas channel 122 and the other end of the coupling channel 168 leads to the exhaust gas channel 70.

Although the coupling channels 162, 164, 166, and 168 are provided in one connecting pipe 8, these channels 162, 164, 166, and 168 may be provided in separate tube materials and the tube materials may be bundled together. It is preferable that the connecting pipe 8 is made of the same materials as that of the base plate 28, the lower frame 30, the base plate 102, and the lower frame 104 joined thereto from the viewpoint of airtightness.

The pathways of the channels provided inside of the supply and discharge part 2, the high-temperature reaction part 4, the low-temperature reaction part 6, and the connecting pipe 8 are as shown in FIGS. 13 and 14. Here, the correspondence relationships between FIGS. 13 and 14 and FIG. 4 will be described. The introduction channel for vaporization 14 corresponds to the channel of the vaporizer 502, the reforming channels 116, 118, and 128 correspond to the channel of the first reformer 506, the reforming channel 150 corresponds to the channel of the second reformer 510, the part from the start point of the channel for removing carbon monoxide 84 to the end point of the channel for removing carbon monoxide 46 corresponds to the channel of the carbon monoxide remover 512, the combustion channel 26 corresponds to the channel of the first combustor 504, and the combustion chambers 138, 140 correspond to the combustion chamber of the second combustor 508.

As shown in FIGS. 2 and 5, an insulating film of silicon nitride, silicon oxide, or the like is formed on the entire of the lower face of the low-temperature reaction part 6, i.e., the lower face of the base plate 28, the lower face of the high-temperature reaction part 4, i.e., the lower face of the base plate 102, and the lower face of the connecting pipe 8. A heating wire 170 is provided under the insulating film at the low-temperature reaction part 6 side in a zig-zag pattern. Further, a heating wire 172 is provided under the insulating film from the low-temperature reaction part 6 through the connecting pipe 8 to the high-temperature reaction part 4 in a zig-zag pattern. The heating wire 172 is provided under the insulating film located from the low temperature reaction part 6 to the high temperature reaction part 6 via the connection pipe 8. An insulating film of silicon nitride, silicon oxide, or the like is also formed on the side surface of the external circulation pipe 10 and the surfaces of the combustion plates 12, and a heating wire 174 is provided from the lower face of the low-temperature reaction part 6 through the surfaces of the combustion plates 12 to the side surface of the external circulation pipe 10. The heating wires 170, 172, 174 are formed by stacking an anti-diffusion layer and a heat generation layer in this order from the insulating film side. The heat generation layer is made of a material having the lowest resistivity in the three layers (e.g., Au). When voltages are applied to the heating wires 170, 172, 174, current flows intensively to generate heat. It is preferable that the anti-diffusion layer is made of a material which makes the material of the heat generation layer hard to cause thermal diffusion to the anti-diffusion layer and the material of the anti-diffusion layer hard to cause thermal diffusion to the heat generation layer, and is a material having relatively high melting point and low reactivity (e.g., W). The adhesion layer may be provided between the insulating film and the anti-diffusion layer when the anti-diffusion layer is low in adhesion to the insulating film and easily peeled. The adhesion layer may be made of a material superior in adhesion to both the anti-diffusion layer and the insulating film (e.g., Ta, Mo, Ti, Cr). The heating wire 170 heats the low-temperature reaction part 6 at the activation, the heating wire 172 heats the high-temperature reaction part 4 and the connecting pipe 8 at the activation, and the heating wire 174 heats the vaporizer 502 and the first combustor 504 of the supply and discharge part 2. Then, when the second combustor 508 is in combustion of the offgas containing hydrogen from the fuel cell, the heating wire 172 heats the high-temperature reaction part 4 and the connecting pipe 8 as an aid to the second combustor 508. Similarly, when the first combustor 504 is in combustion of the offgas containing hydrogen from the fuel cell, the heating wire 170 heats the low-temperature reaction part 6 as an aid to the first combustor 504.

Further, since the electric resistances of the heating wires 170, 172, 174 change depending on temperature, they also function as temperature sensors which read temperature from the resistance variation. Specifically, the electric resistances of the heating wires 170, 172, 174 are proportional to temperature.

All ends of the heating wires 170, 172, 174 are located on the lower face of the base plate 28, and these ends are arranged so as to surround the combustion plates 12. Lead wires 176, 178 as lead wires are connected to both ends of the heating wire 170, respectively, lead wires 180 and 182 are connected to both ends of the heating wire 172, respectively, and third lead wires 184, 186 are connected to both ends of the heating wire 174, respectively. In FIG. 3, for better view of the drawing, illustration of the heating wires 170, 172, 174 and the lead wires 176, 178, 180, 182, 184, 186 is omitted.

Next, a heat insulating structure to suppress heat loss in the microreactor module 1 will be described.

Figure 15:
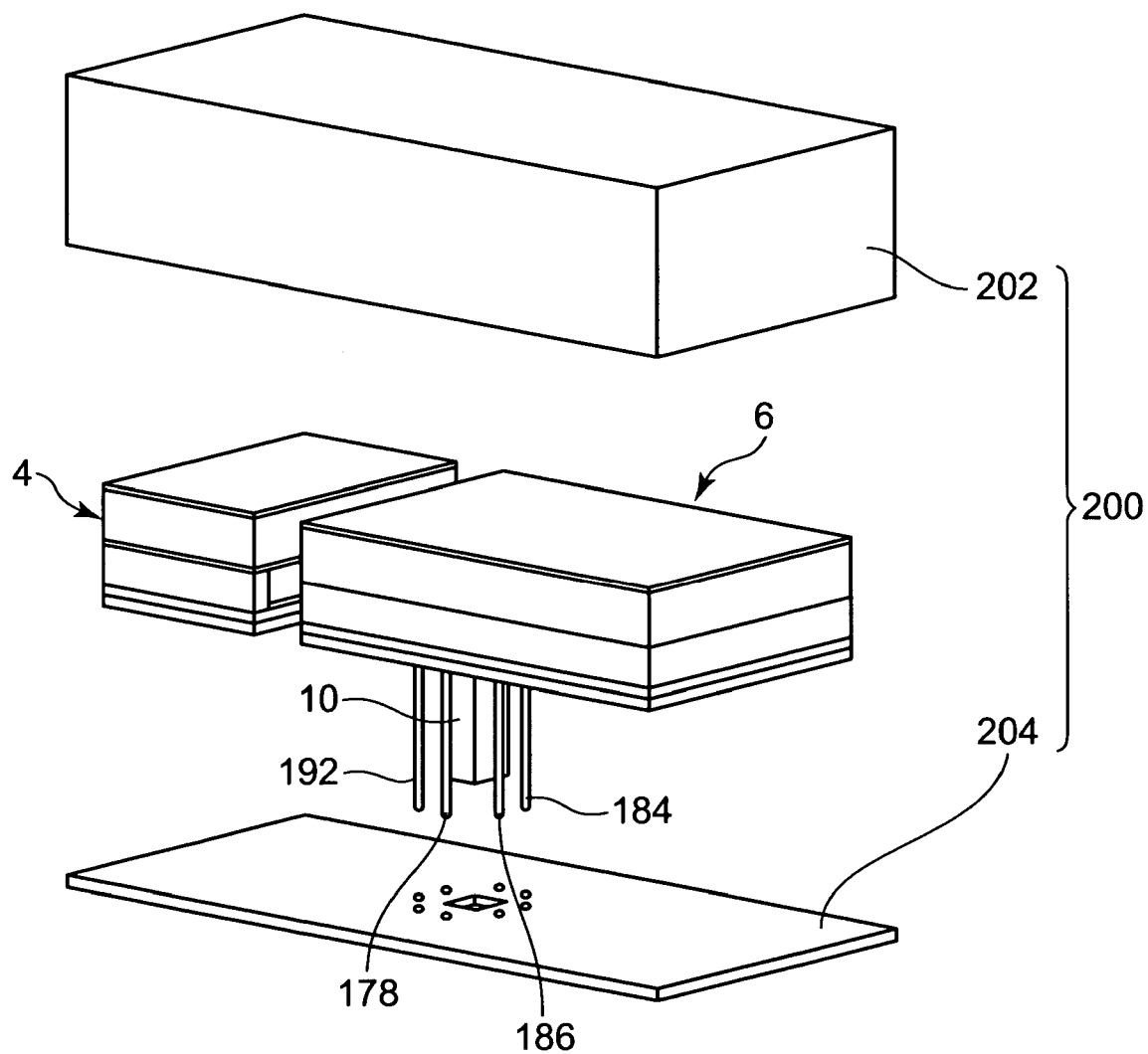
FIG. 15 is an exploded perspective view of a heat insulating package covering the microreactor module 1.

FIG. 15 is an exploded perspective view of a heat insulating package covering the microreactor module.

Figure 16:
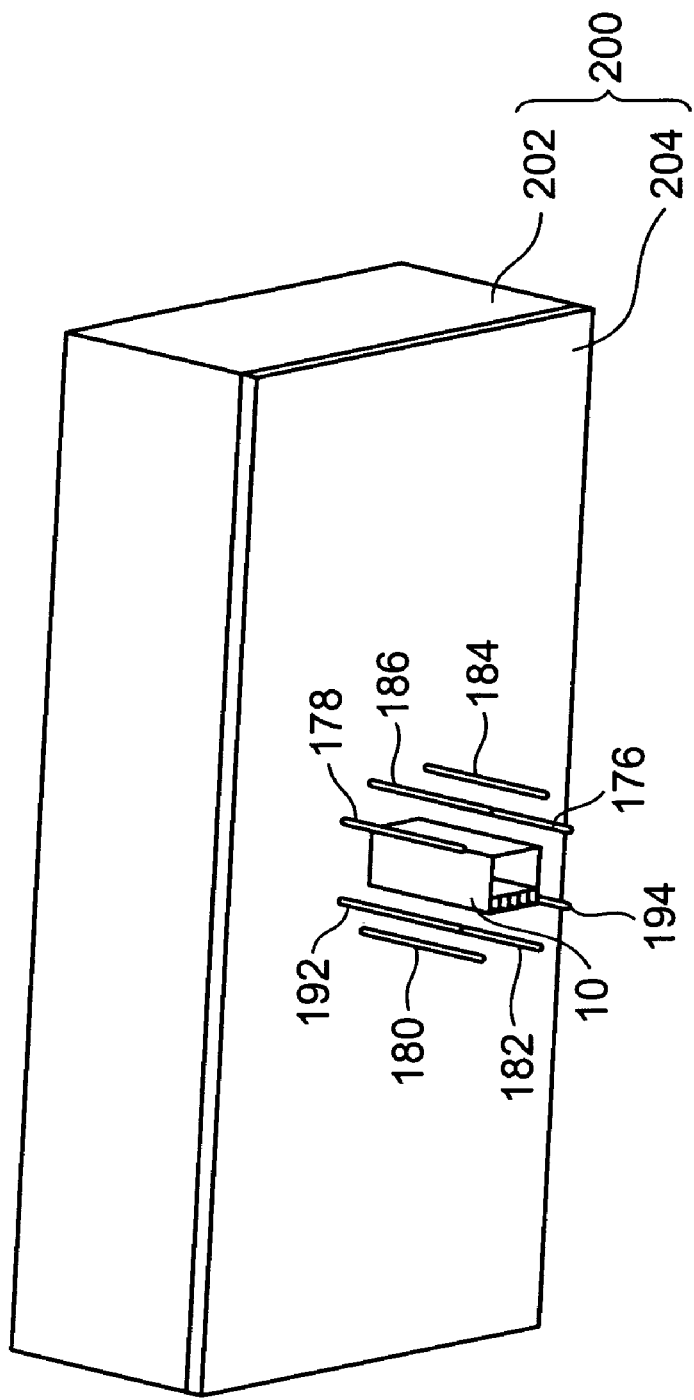
FIG. 16 is a perspective view of the heat insulating package shown seen diagonally below.

FIG. 16 is a perspective view of the heat insulating package seen from diagonally below.

As shown in FIGS. 15 and 16, a heat insulating package 200 covers the above microreactor module 1 wholly, and the high-temperature reaction part 4, the low-temperature reaction part 6 and the connecting pipe 8 are accommodated in the heat insulating package 200. The heat insulating package 200 includes a rectangular box 202 with a lower face opened, and a closing plate 204 which closes the opening of the lower face of the box 202. The base plate 204 is joined to the box 202 and sealed with a glass material or an insulating sealing material. Both the box 202 and the closing plate 204 are made of a sheet-like metal material such as stainless steel, and metal reflection films of aluminum, gold, silver or the like may be formed on the interior surfaces thereof. When such metal reflection films are formed, they can suppress heat loss due to the radiation from the supply and discharge part 2, the high-temperature reaction part 4, the low-temperature reaction part 6, and the connecting pipe 8.

A plurality of through holes penetrates the closing plate 204. The external circulation pipe 10 and the lead wires 176, 178, 180, 182, 184, 186, 192 and 194 are inserted into respective through hole, and a part of each member is exposed to outside from the heat insulating package 200. In order to prevent air from braking into the heat insulating package from the externally exposed portions, the external circulation pipe 10, the lead wires 176, 178, 180, 182, 184 and 186 and the through hole of the closing plate 204 are connected or sealed with glass material, insulating sealing material or the like. The inner space 201 of the heat insulating package 200 is sealed and vacuumed so that the internal pressure of the package is 1 Torr or less. As such, the inner space becomes vacuum condition and thus a vacuum heat insulating structure. By doing so, heat of the microreactor module 1 is prevented from propagating to outside, and heat loss can be suppressed.

The external circulation pipe 10 protrudes both inside and outside of the heat insulating package 200. Thus, inside the heat insulating package 200, the external circulation pipe 10 stands against the closing plate 204 as a strut. The high-temperature reaction part 4, low-temperature reaction part 6 and connection pipe 8 are supported with the external circulation pipe 10 so as to be separated from inner surface of the heat insulating package 200. That is, distance B between a plane facing with the inner surface of the heat insulating package 200 and the inner surface of the heat insulating package 200 is configured to be about 1 mm. It is preferable that the external circulation pipe 10 is connected with a lower plane of the low-temperature reaction part 6 at the gravity center of the integral of the high-temperature reaction part 4, low temperature reaction part 6 and connection pipe 8 in a plan view.

Next, in the microreactor module 1 of the present embodiment, a getter material 188 to improve degree of vacuum in the inner space of the heat insulating package 200 is installed in the heat insulating package 200. The getter material 188 is activated by heat to absorb surrounding micro particles, i.e. shows absorption behavior. The getter material 188 absorbs residual gas left in the inner space of the heat insulating package 200, gas leaked from the microreactor module 1 to the inner space of the heat insulating package 200 and gas braking in from outside into the heat insulating package 200, so as to improve degree of vacuum in the inner space of the heat insulating package 200.

Figure 17:
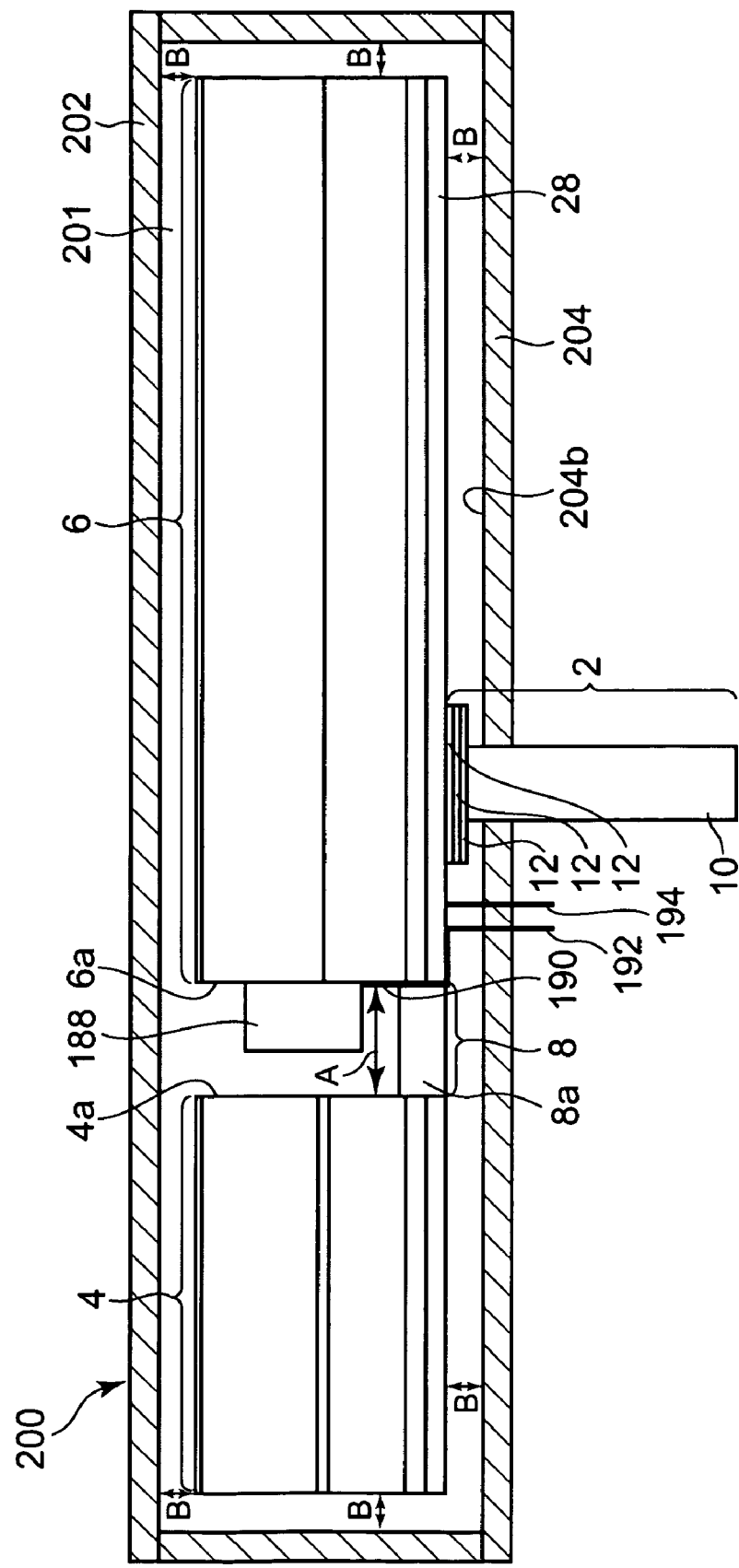
FIG. 17 is a side sectional view showing one installation example of the getter material in the microreactor module of the present embodiment.
Figure 18:
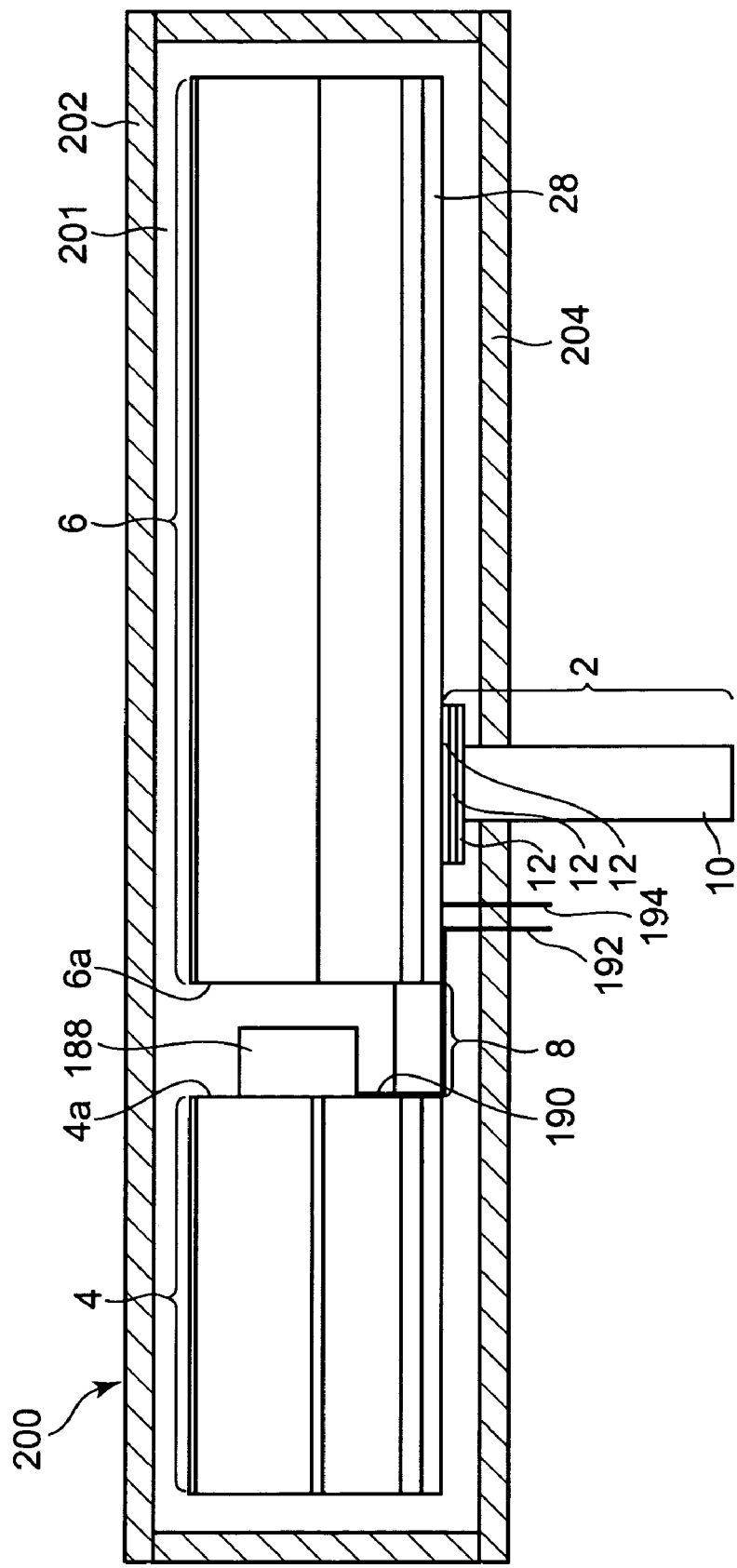
FIGS. 18 to 20 are side sectional views showing other installation example of the getter material of FIG. 17.
Figure 19:
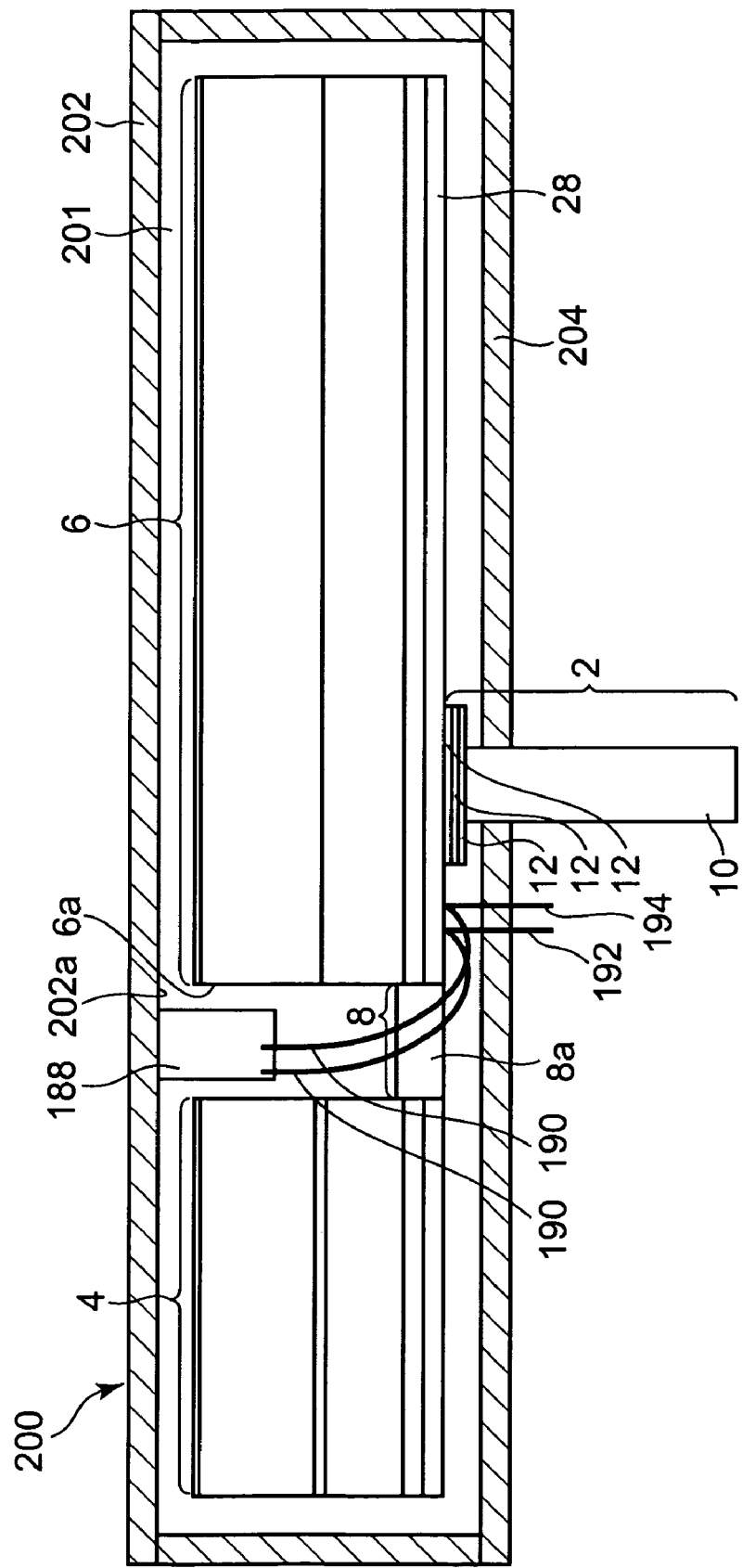
Figure 20:
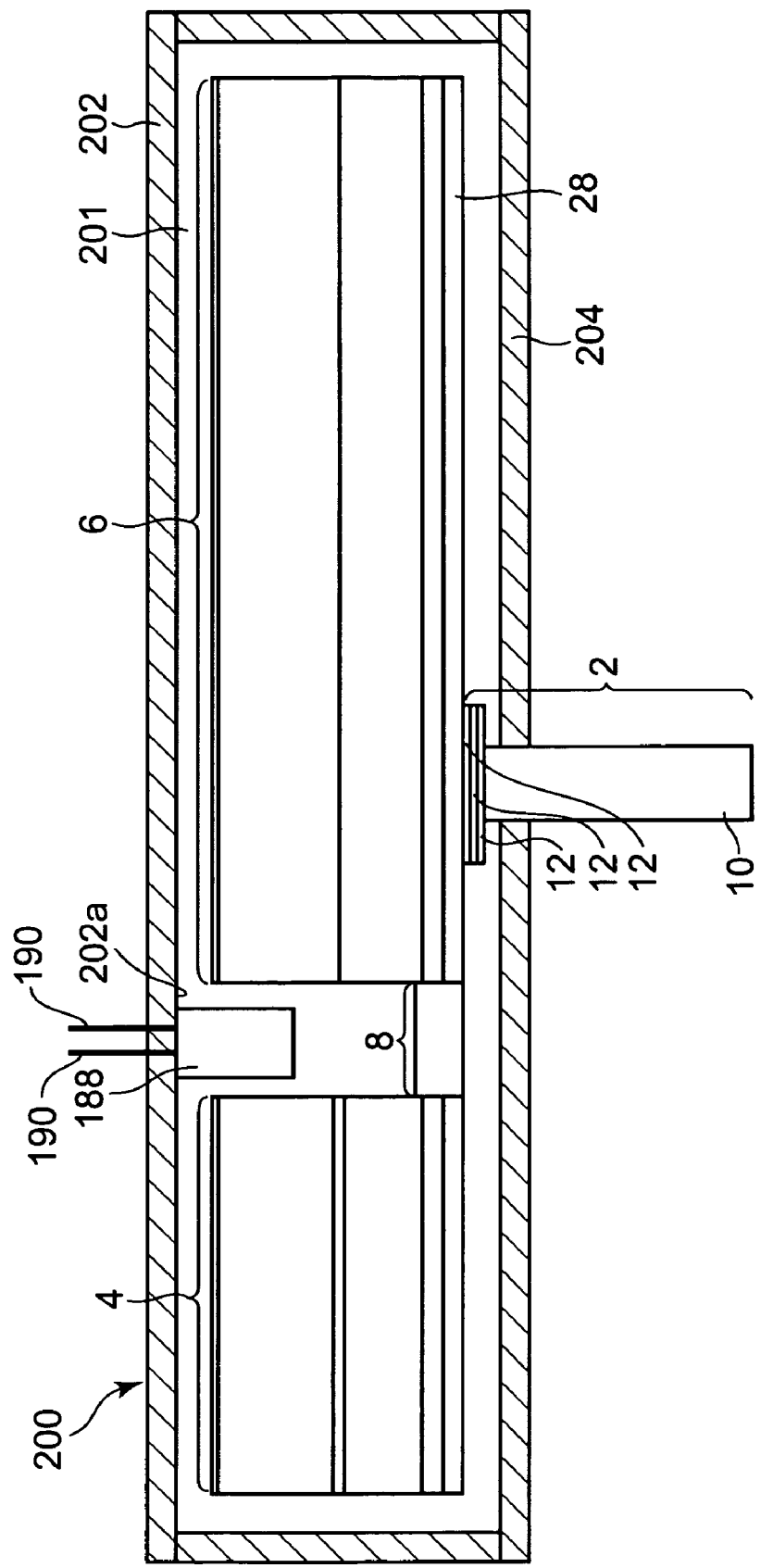

FIG. 17 is a side sectional view showing one installation example of the getter material 188 in the microreactor module 1 of the present embodiment, and FIGS. 18 to 20 are side sectional views showing other installation examples of the getter material 188. The getter material 188 is installed in the inner space 201 of the heat insulating package 200, and at least a part of the getter material 188 is installed in a space including a gap between the high-temperature reaction part 4 and low temperature reaction part 6.

The getter material 188 is, for example as shown in FIGS. 3, 5 and 17, installed to the gap between the high-temperature reaction part 4 and low-temperature reaction part 6, and on a side wall 6a facing with the high-temperature reaction part 4 among the side wall 6 of the low-temperature reaction part 6. The getter material 188 is located above the connection pipe 8. The distance A of the gap between the high-temperature reaction part 4 and low-temperature reaction part 6 (=length of the connection pipe 8) is, for example, about 3 mm.

A heater such as an electric heating material is provided with the getter material 188, and a wire 190 is connected to the heater. The wire 190 is formed downwardly along with the side wall 6a of the low-temperature reaction part 6. At the surrounding of the combustor plate 12, the wire 190 is located on the lower side of the base plate 28 and the both ends thereof are connected to lead wires 192 and 194 respectively.

An alloy principally comprising zirconium, barium, titanium or vanadium can be given as a material of the getter material 188. Both ends of the wire 190 are connected to the heater of the getter material 188 and the lead wires 192 and 194. In FIG. 3, illustration of the lead wires 192 and 194 is omitted to improve visualization of the figure.

According to the above description, the getter material 188 is provided on the side wall 6a of the low-temperature reaction part 6. However, the position of the getter material is not limited specifically, as long as the position is located between the low-temperature reaction part and high-temperature reaction part within the inner space 201 of the heat insulating package 200. For example, as shown in FIG. 18, the getter material may be provided on a wall 4a of the high-temperature reaction part 4 facing with the low-temperature reaction part 6. In this case, the wire 190 may be formed downwardly along with the side wall 4a of the high-temperature reaction part 4 to the base plate 28 via a surface 8a of the connection pipe 8.

As shown in FIGS. 19 and 20, the getter material 188 may be provided on upper inner surface of the heat insulating package 200 (inner surface of a rectangular box 202) corresponding to the gap between the high-temperature reaction part 4 and low-temperature reaction part 6. Such configuration is advantageous in manufacturing, because the getter material 188 can be previously installed to the heat insulating package 200. In the configuration shown in FIG. 19, the wire 190 of the getter material 188 is not along with the side wall 6a of the low-temperature reaction part 6, but reaches lower surface of the base plate 28 at the surrounding of the combustor plate 12 from lower side of the getter material 188 via the surface 8a of the connection pipe 8, and is connected to the lead wires 192 and 194. In the configuration shown in FIG. 20, the wire 190 of the getter material 188 is not wired in the inner space 201 of the heat insulating package 200 but is directly drawn outside the heat insulating package 200. In this configuration, wiring work is facilitated.

Further, although one getter material 188 is provided in the above embodiments, the number of the getter material is not limited. For example, a plurality of the getter material may be provided to different positions. This configuration is preferable in the point that degree of vacuum can be improved repeatedly by activating unused getter material 188 when degree of vacuum in the inner space 201 gets lower. The position of the getter material 188 is not especially limited, as long as the position is in the inner space 201 of the heat insulating package 200 and in the space including the gap between the high-temperature reaction part 4 and low-temperature reaction part 6.

Next, operation of the microreactor module 1 will be described.

First, voltage is applied between the lead wires 192 and 194, and the getter material is heated with the heater so to be activated. Thereby, residual gas in the heat insulating package 200 is absorbed to the getter material 188. Thus, degree of vacuum in the heat insulating package 200 increases and heat insulating efficiency increases.

In the case where the getter material 188 is not used after it is once activated to improve degree of vacuum in the heat insulating package 200, the wire is preferably cut between the base plate 28 which is lower wall of the low-temperature reaction part 6 and an inner surface 204b of the closing plate 204 of the heat insulating package 200 in order to prevent heat energy of the high-temperature reaction part 4 and low-temperature reaction part 6 from being released to outside. As for the method to cut, for example, the wiring may be burn off by applying overcurrent to the wire 190 to heat it.

Further, when a voltage is applied between the first lead wires 176 and 178, the heating wire 170 generates heat and the low-temperature reaction part 6 is heated. When a voltage is applied between the lead wires 180 and 182, the heating wire 172 generates heat and the high-temperature reaction part 4 is heated. When a voltage is applied between the lead wires 184 and 186, the heating wire 174 generates heat and the supply and discharge part 2, mainly the upper part of the external circulation pipe 10 is heated. Since the supply and discharge part 2, the high-temperature reaction part 4, the low-temperature reaction part 6, and the connecting pipe 8 are made of metal materials, heat easily conducts among them. The temperatures of the supply and discharge part 2, the high-temperature reaction part 4, and the low-temperature reaction part 6 are measured by a control device measuring the potentials or currents and voltages of the heating wires 170, 172, and 174. The measured temperature is fed back to the control device and the output voltages of the heating wires 170, 172, and 174 are controlled. Thereby, the temperature control of the supply and discharge part 2, the high-temperature reaction part 4, and the low-temperature reaction part 6 is performed.

In the condition where the supply and discharge part 2, the high-temperature reaction part 4, and the low-temperature reaction part 6 are heated by the heating wires 170, 172, and 174, when the liquid mixture of the liquid fuel and water is continuously or intermittently supplied to the introduction channel for vaporization 14 by an external pump or the like, the liquid mixture is absorbed by the liquid absorbing material and the liquid mixture penetrates upwardly in the introduction channel for vaporization 14 because of a capillary phenomenon. Since the channel is filled with the liquid absorbing material to the height of the combustor plates 12, the liquid mixture within the liquid absorbing material is vaporized, and the gas mixture of the fuel and water evaporates from the liquid absorbing material. Since the liquid mixture vaporizes in the liquid absorbing material, bumping can be suppressed and vaporization is stably performed.

Then, the gas mixture evaporated from the liquid absorbing material passes through the through hole 52, the gas mixture channel 38, the coupling channel 162, and the supply channel 114, and flows into the first reformer 506 (the reforming channels 116, 118, and 128). Then, the gas mixture flows into the second reformer 510 (the reforming channel 150). While the gas mixture is flowing in the reforming channels 116, 118, 128, 150, the gas mixture is heated and reacts with catalysts, hydrogen gas and the like are generated. When the fuel is methanol, see the above reaction formulas (1), (2).

The gas mixture (containing hydrogen gas, carbon dioxide gas, carbon monoxide gas and the like) generated in the first reformer 506 and the second reformer 510 passes through the well holes 156, 144, 130, 124, the discharge channel 115, and the coupling channel 164, and flows into the mixing channel 40. On the other hand, air is supplied by a pump or the like to the air introduction channel 16 flows into the mixing channel 40, the gas mixture of hydrogen gas and the like and air are mixed.

Then, the gas mixture containing air, hydrogen gas, carbon monoxide gas, carbon dioxide gas and the like passes from the mixing channel 40 through the well holes 66, 82, 88 and flows into the carbon monoxide remover 512 (from the channel for removing carbon monoxide 84 to the channel for removing carbon monoxide 46). While the gas mixture is flowing from the channel for removing carbon monoxide 84 to the channel for removing carbon monoxide 46, carbon monoxide gas in the gas mixture is selectively oxidized and the carbon monoxide gas is removed. Here, the carbon monoxide gas does not uniformly react of the path from the channel for removing carbon monoxide 84 to the channel for removing carbon monoxide 46, but the reaction rate of carbon monoxide gas is greater at the downstream side (mainly from the channel for removing carbon monoxide 80 to the channel for removing carbon monoxide 46) of the pathway from the channel for removing carbon monoxide 84 to the channel for removing carbon monoxide 46. Since the oxidization reaction of carbon monoxide gas is an endothermic reaction, heat is generated mainly in the part from the channel for removing carbon monoxide 80 to the channel for removing carbon monoxide 46. Since the external circulation pipe 10 is located below this part, the heat caused by the oxidization reaction of carbon monoxide gas is efficiently used for the vaporization heat of water and fuel in the vaporizer 502 together with the heat of the first combustor 504.

Then, the gas mixture from which carbon monoxide has been removed is supplied to the fuel electrode and the like of the fuel cell through the through hole 54 and the hydrogen discharge channel 24. In the fuel cell, electricity is generated by the electrochemical reaction of the hydrogen gas supplied from the hydrogen gas discharge channel 24, and the offgas containing unreacted hydrogen gas and the like is discharged from the fuel cell.

The above described operation is an operation in the early stage, and the liquid mixture is continuously supplied to the introduction channel for vaporization 14 during power generation in the following stages. Then, air is mixed in the offgas discharged from the fuel cell, and the gas mixture (hereinafter, referred to as "combustion mixture") is supplied to the combustion mixture introduction channel 22 and the combustion mixture introduction channel 18. The combustion mixture supplied to the combustion mixture introduction channel 22 flows into the combustion channel 26 of the first combustor 504, and the combustion mixture burns to generate combustion heat, since the combustion channel 26 surrounds the external circulation pipe 10 below the low-temperature reaction part 6, the combustion heat heats the external circulation pipe 10 and the low-temperature reaction part 6. Accordingly, electric power supplied to the heating wires 170, 174 can be reduced and the use efficiency of energy becomes higher.

On the other hand, the combustion mixture supplied to the combustion mixture introduction channel 18 flows into the combustion chambers 138 and 140 of the second combustor 508, and burns. Thereby, combustion heat is generated and heats the first reformer 506 and the second reformer 510, because the first reformer 506 is disposed under the combustion chambers 138 and 140, and the second reformer 510 is disposed on the combustion chambers 138 and 140. Heat can be efficiently propagated in the surface direction because the second combustor 508 is sandwiched with the first reformer 506. Further, the second reformer 510 from above and below and the heat loss is low because the second combustor 508 is sealed with the heat insulating package 200, the part exposed to the space is small. Thus, electric power supplied to the heating wire 172 can be reduced and the use efficiency of energy becomes higher.

A part of the liquid fuel stored in the fuel container may be vaporized and the combustion mixture of the vaporized fuel and air may be supplied to the combustion mixture introduction channels 18 and 22.

In the condition where the liquid mixture is supplied to the introduction channel for vaporization 14 and the combustion mixture is supplied to the combustion mixture introduction channels 18 and 22, the control device controls the voltages applied to the heating wires 170, 172, 174, the pump and the like while the control device measures the temperature by the resistance of the heating wires 170, 172 and 174. The control device controls the pump so that the flow of the combustion mixture supplied to the combustion mixture introduction channels 18 and 22 is controlled, and thereby, the amounts of combustion heat of the combustors 504 and 508 are controlled. As such, the control device controls the heating wires 170, 172, 174 and the pump do that the temperature control of the high-temperature reaction part 4, the low-temperature reaction part 6, and the supply and discharge part 2 is performed, respectively. Here, the temperature control is performed so that the high-temperature reaction part 4 may reach 250° C. to 400° C., preferably 300° C. to 380° C., the low-temperature reaction part 6 may reach temperature lower than that of the high-temperature reaction part 4, specifically, 120° C. to 200° C., more preferably 140° C. to 180° C.

Next, an example of specific size and material of each part in the reactor of the present invention will be described. The high-temperature reaction part 4 is, for example, formed to be about 16 mm in width, 10 mm in length and 6 mm in height. The height of the second combustor is, for example, made to be about 0.3 mm. The connecting pipe 8 is, for example, formed to be about 3 mm in length and 1 mm in height and width. The low-temperature reaction part 6 is, for example, formed to be about 16 mm in width, 23 mm in length and 6 mm in height. Thereby, space of about 3 mm is formed between the high-temperature reaction part 4 and low temperature reaction part 6. The getter material 188 is provided to the space. The external circulation pipe 10 is, for example, 7 to 8 mm in length and 2 to 3 mm in longitudinal and lateral directions. The heat insulating package 200 is, for example, is formed to be about 9 to 10 mm in height, 20 mm in width and 40 mm in length. The metal material forming the high-temperature reaction part 4, low-temperature reaction part 6, connection pipe 8, external circulation pipe 10, combustor plate 12 and the like is, for example, stainless steel SUS 304 having about 0.1 to 0.2 mm thickness. The heat insulating package 200 is, for example, stainless steel SUS 304 having about 0.5 mm thickness. When the reactor is configured as described above and electric power of the electric heating wires 170 and 172 is set to 15 W and 25 W respectively, the high-temperature reaction part 4 and low-temperature reaction part 6 can be heated up to 375° C. and 150° C. in 9 to 10 seconds. Thus, it is possible to start-up the reactor in comparatively short time.

Figure 21:
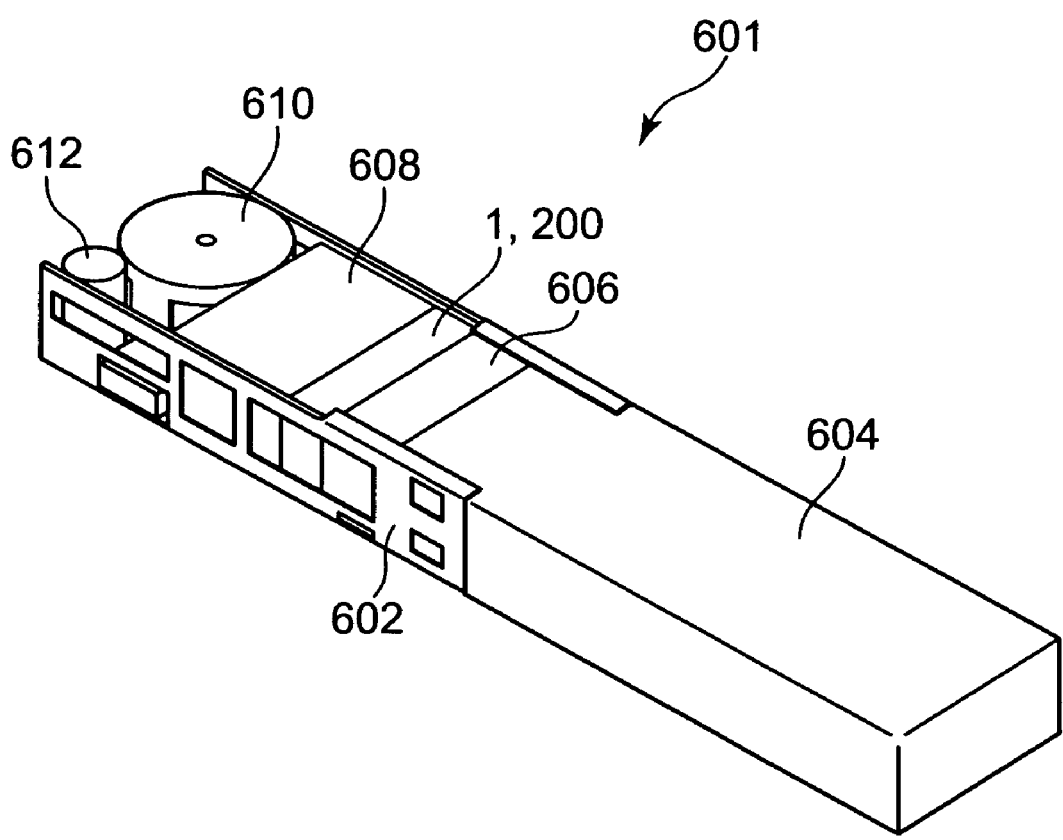
FIG. 21 is a perspective view showing one example of a power generation unit comprising the microreactor module of the present embodiment.
Figure 22:
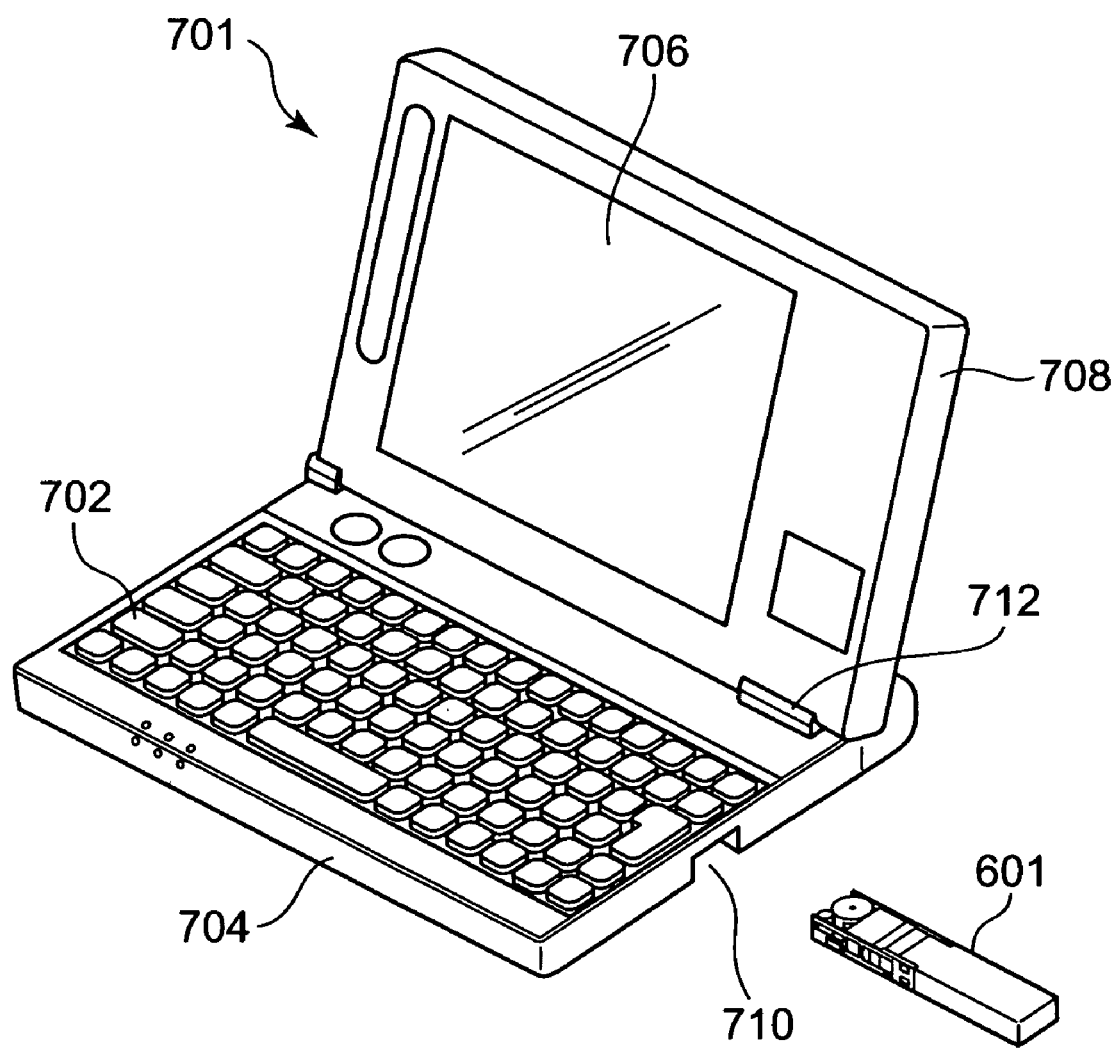
FIG. 22 is a perspective view showing one example of electronic equipment using the power generation unit as a power source.

Next, schematic constitution of a power generation unit 601 comprising the microreactor module 1 of the present embodiment will be described. FIG. 21 is a perspective view showing one example of the power generation unit 601 comprising the microreactor module 1. FIG. 22 is a perspective view of one example of electronic equipment 701 using the power generation unit 601 as power supply. As shown in FIG. 21, the above described microreactor module can be used with being incorporated in a power generation unit 601. The power generation unit 601 includes, for example, a frame 602, a fuel container 604 detachable from the frame 602, a flow rate control unit 606 having a channel, pump, flow sensor, valve and the like, the microreactor module 1 accommodated in the heat insulating package 200, a power generation module 608 having a fuel cell, a humidifier for humidifying the fuel cell, a collector for collecting by-products generated in the fuel cell, an air pump 610 for supplying air (oxygen) to the microreactor module 1 and the power generation module 608, a power supply unit 612 having an external interface for electrically connecting to a secondary cell, a DC-DC converter and external equipment driven by output of the power generation unit 601. Since the flow rate control unit 606 supplies the gas mixture of water and liquid fuel in the fuel container 604 to the microreactor module 1, a hydrogen-rich gas is generated as described above, the hydrogen-rich gas is formed and supplied to the fuel electrode of the power generation module 608, and the generated electricity is stored in the secondary cell of the power supply unit 612.

As shown ion FIG. 22, the electronic equipment 701 is portable electronic equipment, particularly, a notebook personal computer. The electronic equipment 701 includes a lower casing 704 having an arithmetic processing circuit composed of CPU, RAM, ROM, and other electronic parts and a keyboard 702 and an upper casing 708 having a liquid crystal display 706. The lower casing 704 and the upper casing 708 are coupled by a hinge part and arranged so that the equipment can be folded with the upper casing 708 lapping over the lower casing 704 and the keyboard 702 facing with the liquid crystal display 706. A mounting part 710 for mounting the power generation unit 601 is recessed from the right side face to the bottom face of the lower casing 704. When the power generation unit 601 is mounted on the mounting part 710, the electronic equipment 701 operates by the electricity of the power generation unit 601.

According to the present embodiment as described above, since the getter material is provided between the high-temperature reaction part 6 and low-temperature reaction part 4 in the inner space 201 of the heat insulating package 200, gas in the inner space 201 is absorbed by the absorption behavior of the getter material 188. Thereby, degree of vacuum is improved, and heat loss occurred in the high-temperature reaction part 4 and low-temperature reaction part 6 can be reduced. Further, it is not necessary to provide a space to dispose the getter material 188 and the space in the heat insulating material 200 is effectively utilized. Thus, it is possible to downsize the reactor.

Further, the getter material 188 is provided on the side wall 6a facing with the high-temperature reaction part 4 among the side walls of the low-temperature reaction part 6, the wire 190 is formed along with the side wall 6a of the low-temperature reaction part 6 and is drawn from lower surface of the base plate 28. Thus, the getter material 188 and wire 190 can be heated with the heat of the low-temperature reaction part 6, which results superior heat efficiency.

Further, according to the embodiment, the inner space of the heat insulating package 200 is heat insulating space, the high-temperature reaction part 4 is spaced from the low-temperature reaction part 6, and the distance from the high-temperature reaction part 4 to the low-temperature reaction part 6 is the length of the connecting pipe 8. Therefore, the pathway of heat conduction from the high-temperature reaction part 4 to the low-temperature reaction part 6 is limited to the connecting pipe 8 and the heat conduction to the low-temperature reaction part 6 which does not require high temperature is restricted. Specifically, since the height and width of the connecting pipe 8 are smaller than those of the high-temperature reaction part 4 and low-temperature reaction part 6, heat conduction through the connecting pipe 8 is minimized. Accordingly, it can be suppressed that heat loss of the high-temperature reaction part 4 as well as the temperature of the low-temperature reaction part 6 rises to higher temperature than the preset temperature. That is, even when the high-temperature reaction part 4 and the low-temperature reaction part 6 are accommodated within one heat insulating package 200, a temperature difference can be produced between the high-temperature reaction part 4 and the low-temperature reaction part 6.

Further, since the coupling channels 162, 164, 166, and 168 are assembled in one connecting pipe 8, stress occurred in the connecting pipe 8 and the like can be reduced. That is, since there is a temperature difference between the high-temperature reaction part 4 and the low-temperature reaction part 6, the high-temperature reaction part 4 expands more than the low-temperature reaction part 6. However, the stress generated in the connecting pipe 8 and the like can be suppressed because the high-temperature reaction part 4 has free ends except the coupling part to the connecting pipe 8. Specifically, the height and width of the connecting pipe 8 are smaller than those the high-temperature reaction part 4 and the low-temperature reaction part 6, and further, the connecting pipe 8 is coupled to the high-temperature reaction part 4 and the low-temperature reaction part 6 at the centers in the width direction of the high-temperature reaction part 4 and the low-temperature reaction part 6. Thus, the generation of stress in the connecting pipe 8, the high-temperature reaction part 4, and the low-temperature reaction part 6 can be suppressed.

Since also the external circulation pipe 10 is coupled between the low-temperature reaction part 6 and the heat insulating package 200, the stress occurred in the external circulation pipe 10 and the like can be reduced.

If the channels 162, 164, 166, and 168 are provided in separate coupling tube materials and the coupling tube materials are spaced each other and spanned between the high-temperature reaction part 4 and the low-temperature reaction part 6, stress occurs in these tube materials, the low-temperature reaction part 6, and the high-temperature reaction part 4 due to the displacement difference between the low-temperature reaction part 6 and the high-temperature reaction part 4. Further, since the temperature difference between high temperature condition and low temperature condition in the high-temperature reaction part 4 is larger than the temperature difference between high temperature condition and low temperature condition in the low-temperature reaction part 6, when the external circulation tube material is provided at the high-temperature reaction part 4 side, the thermal expansion and constriction of the tube material becomes larger than those of the tube material when the external circulation tube material is provided at the low-temperature reaction part 6 side, and therefore, the airtightness within the heat insulating package 200 is easily hindered. In the embodiment, occurrence of such stress is suppressed and airtightness can be finely held.

The external circulation pipe 10 and the lead wires 176, 178, 180, 182, 184, 186, 192, and 194 extend to the outside of the heat insulating package 200, and all of them are coupled to the low-temperature reaction part 6. Accordingly, the direct heat generation from the high-temperature reaction part 4 to the outside of the heat insulating package 200 can be suppressed and the heat loss of the high-temperature reaction part 4 can be suppressed. Therefore, even when the high-temperature reaction part 4 and the low-temperature reaction part 6 are accommodated within one heat insulating package 200, a temperature difference can be produced between the high-temperature reaction part 4 and the low-temperature reaction part 6. Especially, since the introduction channel for vaporization 14, the air introduction channel 16, the combustion mixture introduction channel 18, the exhaust gas discharge channel 20, the combustion mixture introduction channel 22, and the hydrogen gas discharge channel 24 are provided in one external circulation pipe 10, the surface area exposed outside is suppressed, and the heat release to the outside of the heat insulating package 200 can be suppressed, and the heat loss can be suppressed.

Since the lower face of the connecting pipe 8, the lower face of the high-temperature reaction part 4, and the lower face of the low-temperature reaction part 6 are in the same plane, the heating wire 172 can be patterned relatively easily, and disconnection of the heating wire 172 can be suppressed.

Further, since the introduction channel for vaporization 14 of the external circulation pipe 10 is filled with the liquid absorbing material so that the introduction channel for vaporization 14 works as the vaporizer 502, the temperature condition required for vaporization of liquid mixture (for example, a condition in which the upper part of the introduction channel for vaporization 14 is at 120° C.) can be provided while downsizing and simplification of the microreactor module 1 is realized.

Further, since the combustion plates 12 are provided around the external circulation pipe 10 at the upper end of the external circulation pipe 10, and further, the introduction channel for vaporization 14 is filled with the liquid absorbing material to the height of the combustion plates 12, the combustion heat in the first combustor 504 can be efficiently used for vaporization of the liquid mixture.

Further, since the second combustor 508 is sandwiched between the first reformer 506 and the second reformer 510, the combustion heat of the second combustor 508 is evenly propagated to the first reformer 506 and the second reformer 510, and no temperature difference is produced between the first reformer 506 and the second reformer 510.

Since the partition walls which partitions the channels are made relatively thin in any part of the supply and discharge part 2, the high-temperature reaction part 4, the low-temperature reaction part 6, and the connecting pipe 8, the heat capacity of them can be reduced and the supply and discharge part 2, the high-temperature reaction part 4, the low-temperature reaction part 6, and the connecting pipe 8 can be rapidly heated from the room temperature to high temperature in early stage of the operation. Furthermore, the power supplied to the heating wires 170, 172, 174 can be reduced.

What is claimed is:

1. A reactor comprising:
   a first reaction part and a second reaction part, each comprising a reaction channel adapted to have a reactant flow therethrough, wherein the reactant is supplied to the first reaction part and the second reaction part to cause a reaction of the reactant, and the first reaction part and the second reaction part are arranged to form a gap therebetween;
   a heat insulating container covering at least an entirety of the first reaction part, the second reaction part, and the gap, wherein a pressure within an inner space of the heat insulating container including the gap is lower than atmospheric pressure; and
   at least one getter material disposed in a space including the gap in the inner space of the heat insulating container, the getter material being disposed to at least one of a face of the first reaction part at a position corresponding to the gap, and a face of the second reaction part at a position corresponding to the gap;
   wherein:
      the getter material is provided with a heater to heat the getter material so as to activate the getter material;
      the heater comprises an electric heating wire and a lead wire to supply electric power to the electric heating wire;
      the lead wire is wired to penetrate the heat insulating container to reach outside; and
      the reactor further comprises cutting means to cut off the lead wire at a position between a face of the first reaction part or the second reaction part and the inner face of the heat insulating container, after the getter material is heated to be activated.

2. The reactor of claim 1, wherein the heat insulating container comprises a box formed by joining a sheet-like metal material.

3. The reactor of claim 1, wherein each of the first reaction part and the second reaction part comprises a reaction container having a rectangular parallelepiped shape, and the reaction channel in each of the first reaction part and the second reaction part is formed by providing a partition wall to an inside of the reaction container.

4. The reactor of claim 3, wherein the reaction container and the partition wall are formed by joining a sheet-like metal material.

5. The reactor of claim 1, wherein the first reaction part, the second reaction part, and the heat insulating container are box-shaped, one face of the first reaction part is opposed to one face of the second reaction part, and the getter material is disposed to at least one of the face of the first reaction part that is opposed to the second reaction part, and the face of the second reaction part that is opposed to the first reaction part.

6. The reactor of claim 1, wherein the first reaction part is set to a first temperature, and the second reaction part is set to a second temperature which is lower than the first temperature.

7. The reactor of claim 6, further comprising a connection part disposed at the gap, to transport the reactant and a product formed by the reaction between the first reaction part and the second reaction part.

8. The reactor of claim 7, wherein the connection part is formed by joining a sheet-like metal material, and is joined to the first reaction part and the second reaction part.

9. The reactor of claim 7, further comprising a heating part to heat the first reaction part and the second reaction part.

10. The reactor of claim 9, wherein the heating part is disposed to the first reaction part, heats the first reaction part to the first temperature, and heats the second reaction part to the second temperature via the connection part.

11. The reactor of claim 9, wherein the heating part comprises a combustor to combust a gas fuel.

12. The reactor of claim 11, wherein the combustor comprises a catalyst for combustion to promote combustion reaction of the gas fuel.

13. The reactor of claim 9, wherein the heating part comprises an electric heating wire which generates heat when electric power is supplied.

14. The reactor of claim 1, comprising a plurality of the getter materials.

15. The reactor of claim 1, wherein the cutting means applies overcurrent to the lead wire so as to burn off the lead wire.

16. A reactor comprising:
   a first reaction part and a second reaction part, each comprising a reaction channel adapted to have a reactant flow therethrough, wherein the reactant is supplied to the first reaction part and the second reaction part to cause a reaction of the reactant, the first reaction part and the second reaction part are box-shaped and are arranged to form a gap therebetween, and a face of the first reaction part is opposed to a face of the second reaction part at the gap;
   a heat insulating container covering at least an entirety of the first reaction part, the second reaction part, and the gap, wherein the heat insulating container has a rectangular parallelepiped shape, and a pressure within an inner space of the heat insulating container including the gap is lower than atmospheric pressure; and
   at least one getter material disposed to at least one of the face of the first reaction part that is opposed to the second reaction part, and the face of the second reaction part that is opposed to the first reaction part;
   wherein:
      the getter material is provided with a heater to heat the getter material so as to activate the getter material;
      the heater comprises an electric heating wire and a lead wire to supply electric power to the electric heating wire;
      the lead wire is wired to penetrate the heat insulating container to reach outside; and
      the reactor further comprises cutting means to cut off the lead wire at a position between a face of the first reaction part or the second reaction part and the inner face of the heat insulating container, after the getter material is heated to be activated.

17. The reactor of claim 16, wherein the heat insulating container comprises a box formed by joining a sheet-like metal material.

18. The reactor of claim 16, wherein each of the first reaction part and the second reaction part comprises a reaction container having a rectangular parallelepiped shape, and the reaction channel in each of the first reaction part and the second reaction part is formed by providing a partition wall to an inside of the reaction container.

19. The reactor of claim 18, wherein the reaction container and the partition wall are formed by joining a sheet-like metal material.

20. The reactor of claim 16, comprising a plurality of the getter materials.

21. A reactor comprising:
a first reaction part and a second reaction part, each comprising a reaction channel adapted to have a reactant flow therethrough, wherein the reactant is supplied to the first reaction part and the second reaction part to cause a reaction of the reactant, and the first reaction part and the second reaction part are arranged to form a gap therebetween;
a heat insulating container covering at least an entirety of the first reaction part, the second reaction part, and the gap, wherein an inner space of the heat insulating container including the gap has a pressure that is lower than atmospheric pressure; and
at least one getter material disposed in a space including the gap in the inner space of the heat insulating container, the getter material being disposed to at least one of a face of the first reaction part at a position corresponding to the gap, and a face of the second reaction part at a position corresponding to the gap;
wherein the first reaction part is set to a first temperature, and a first reactant is supplied to the first reaction part to form a first product;
wherein the second reaction part is set to a second temperature which is lower than the first temperature, and the first product is supplied to the second reaction part to form a second product;
wherein the first reactant is gas mixture of vaporized water and a fuel whose composition contains a hydrogen atom, and the first reaction part is a reformer to cause a reforming reaction of the first reactant;
wherein the first product contains carbon monoxide, and the second reaction part is a carbon monoxide remover to remove the carbon monoxide contained in the first product by selective oxidation;
wherein:
the getter material is provided with a heater to heat the getter material so as to activate the getter material;
the heater comprises an electric heating wire and a lead wire to supply electric power to the electric heating wire;
the lead wire is wired to penetrate the heat insulating container to reach outside; and
the reactor further comprises cutting means to cut off the lead wire at a position between a face of the first reaction part or the second reaction part and the inner face of the heat insulating container, after the getter material is heated to be activated.

22. The reactor of claim 21, further comprising a vaporizer, wherein water and a liquid fuel whose composition contains a hydrogen atom are supplied to the vaporizer, and the vaporizer vaporizes the water and the liquid fuel to form the gas mixture.

23. The reactor of claim 21, further comprising a connection part disposed at the gap, to transport the reactant and a product formed by the reaction between the first reaction part and the second reaction part.

24. The reactor of claim 23, further comprising a heating part disposed to the first reaction part, to heat the first reaction part to the first temperature, wherein the heating part heats the second reaction part to the second temperature via the connection part.

25. The reactor of claim 24, wherein the heating part comprises a combustor to combust a gas fuel.

26. The reactor of claim 16, wherein the cutting means applies overcurrent to the lead wire so as to burn off the lead wire.

27. The reactor of claim 21, wherein the cutting means applies overcurrent to the lead wire so as to burn off the lead wire.

* * * * *